US012661515B2

(12) United States Patent
Haddock et al.

(10) Patent No.: US 12,661,515 B2
(45) Date of Patent: Jun. 23, 2026

(54) FEATURE SELECTION AND SENSING OPTIMIZATION FOR ADAPTIVE NEUROMODULATION THERAPY

(71) Applicant: Boston Scientific Neuromodulation Corporation, Valencia, CA (US)

(72) Inventors: Andrew James Haddock, Los Angeles, CA (US); Tianhe Zhang, Studio City, CA (US); Satya Venkata Sandeep Avvaru, Minneapolis, MN (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 399 days.

(21) Appl. No.: 18/230,941

(22) Filed: Aug. 7, 2023

(65) Prior Publication Data

US 2024/0058610 A1 Feb. 22, 2024

Related U.S. Application Data

(60) Provisional application No. 63/398,284, filed on Aug. 16, 2022.

(51) Int. Cl.
*A61N 1/36* (2006.01)

(52) U.S. Cl.
CPC ................................. *A61N 1/36139* (2013.01)

(58) Field of Classification Search
None
See application file for complete search history.

(56) References Cited

U.S. PATENT DOCUMENTS 8,606,362 B2 12/2013 He et al.
8,620,436 B2 12/2013 Parramon et al.
(Continued)

FOREIGN PATENT DOCUMENTS

WO WO-2013063111 A1 5/2013
WO WO-2024039538 A1 2/2024

OTHER PUBLICATIONS

"European Application Serial No. 23762070.3, Response to Communication pursuant to Rules 161 and 162 EPC filed Sep. 22, 2025", 9 pgs.

(Continued)

*Primary Examiner* — Benjamin J Klein
*Assistant Examiner* — Willow Grace Welch
(74) *Attorney, Agent, or Firm* — Schwegman Lundberg & Woessner, P.A.

(57) ABSTRACT

Systems and methods for closed-loop control of electrostimulation based on signal features derived from evoked neural activities are disclosed. A system comprises an electrostimulator to deliver a stimulation therapy, a sensing circuit to sense an evoked response induced by the stimulation therapy, and a controller circuit to identify, from a plurality of candidate signal features, a target signal feature that satisfies a performance criterion for distinguishing a first stimulation effect according to a first stimulation setting from a second stimulation effect according to a different second stimulation setting. The target signal feature can be identified based on evaluations of a discrimination metric for each of the candidate signal features. The controller circuit can determine a value of the target signal feature from the sensed evoked response, and control the electrostimulator to adjust the stimulation therapy based on the value of the target signal feature.

18 Claims, 16 Drawing Sheets

(56) References Cited

U.S. PATENT DOCUMENTS

| | | | |
|---|---|---|---|
| 9,259,574 B2 | 2/2016 | Aghassian et al. | |
| 2006/0247687 A1* | 11/2006 | Swerdlow | A61N 1/371 |
| | | | 607/4 |
| 2011/0257708 A1* | 10/2011 | Kramer | A61N 1/36053 |
| | | | 607/62 |
| 2013/0253350 A1* | 9/2013 | Li | A61B 5/304 |
| | | | 600/509 |
| 2015/0080982 A1 | 3/2015 | Van Funderburk | |
| 2015/0231402 A1 | 8/2015 | Aghassian | |
| 2015/0360038 A1 | 12/2015 | Zottola et al. | |
| 2016/0144183 A1 | 5/2016 | Marnfeldt | |
| 2018/0071513 A1 | 3/2018 | Weiss et al. | |
| 2018/0071520 A1 | 3/2018 | Weerakoon et al. | |
| 2018/0085584 A1* | 3/2018 | Thakur | A61N 1/36139 |
| 2019/0022397 A1* | 1/2019 | Srivastava | A61N 1/36139 |
| 2021/0008371 A1 | 1/2021 | Annecchino | |
| 2022/0016413 A1 | 1/2022 | John et al. | |
| 2022/0172838 A1* | 6/2022 | Besanson | G16H 50/20 |
| 2023/0144885 A1 | 5/2023 | Zhang et al. | |

OTHER PUBLICATIONS

"International Application Serial No. PCT/US2023/029612, International Preliminary Report on Patentability mailed Feb. 27, 2025", 6 pgs.
"International Application Serial No. PCT/US2023/029612, International Search Report mailed Nov. 9, 2023", 4 pgs.
"International Application Serial No. PCT/US2023/029612, Written Opinion mailed Nov. 9, 2023", 4 pgs.

* cited by examiner

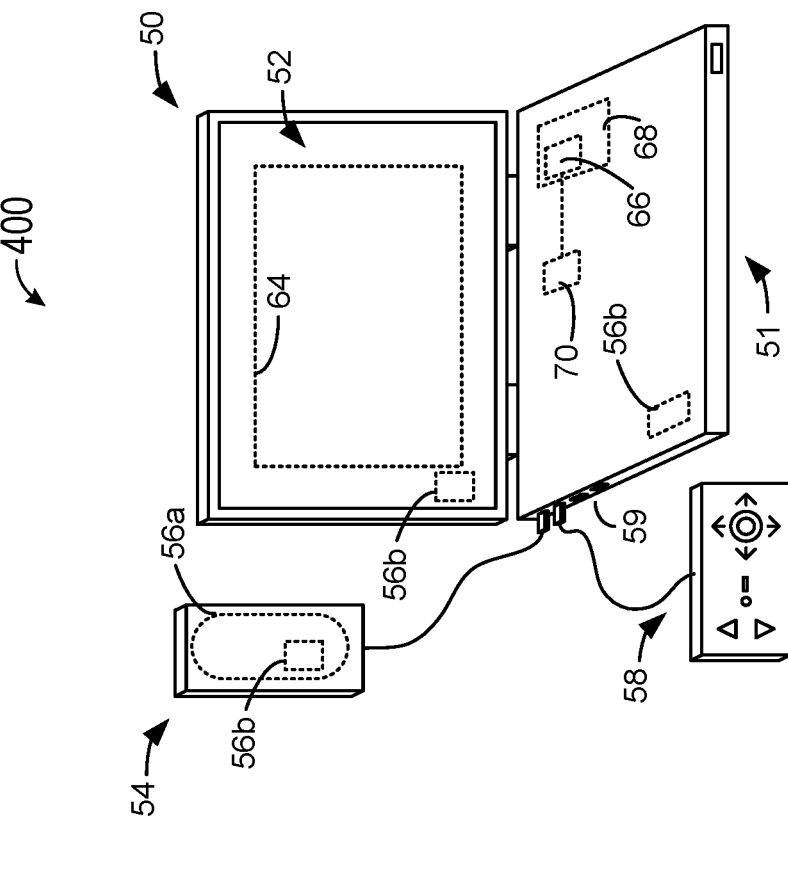
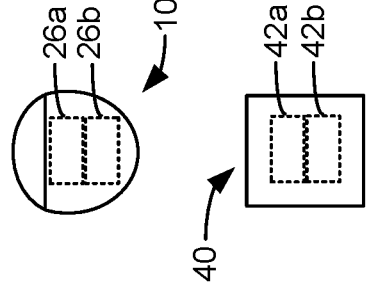
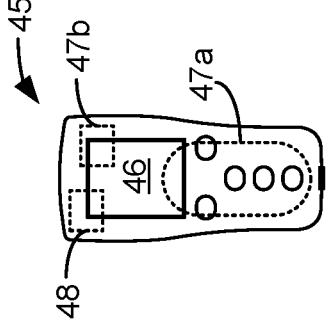
FIG.4

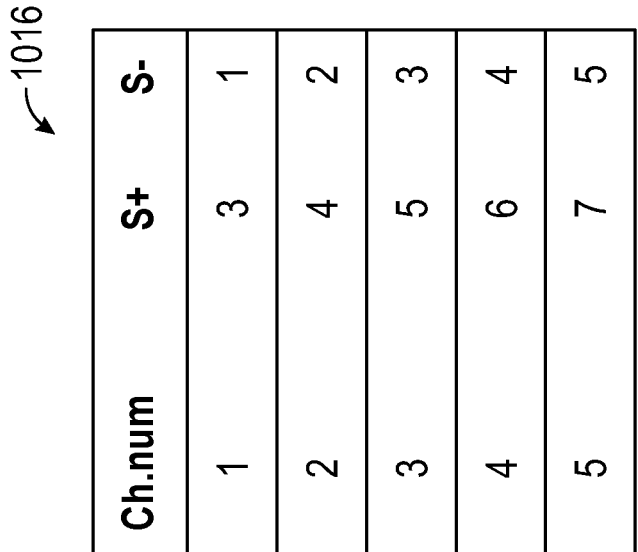
| Ch.num | S+ | S- |
|--------|----|----|
| 1 | 3 | 1 |
| 2 | 4 | 2 |
| 3 | 5 | 3 |
| 4 | 6 | 4 |
| 5 | 7 | 5 |
1016
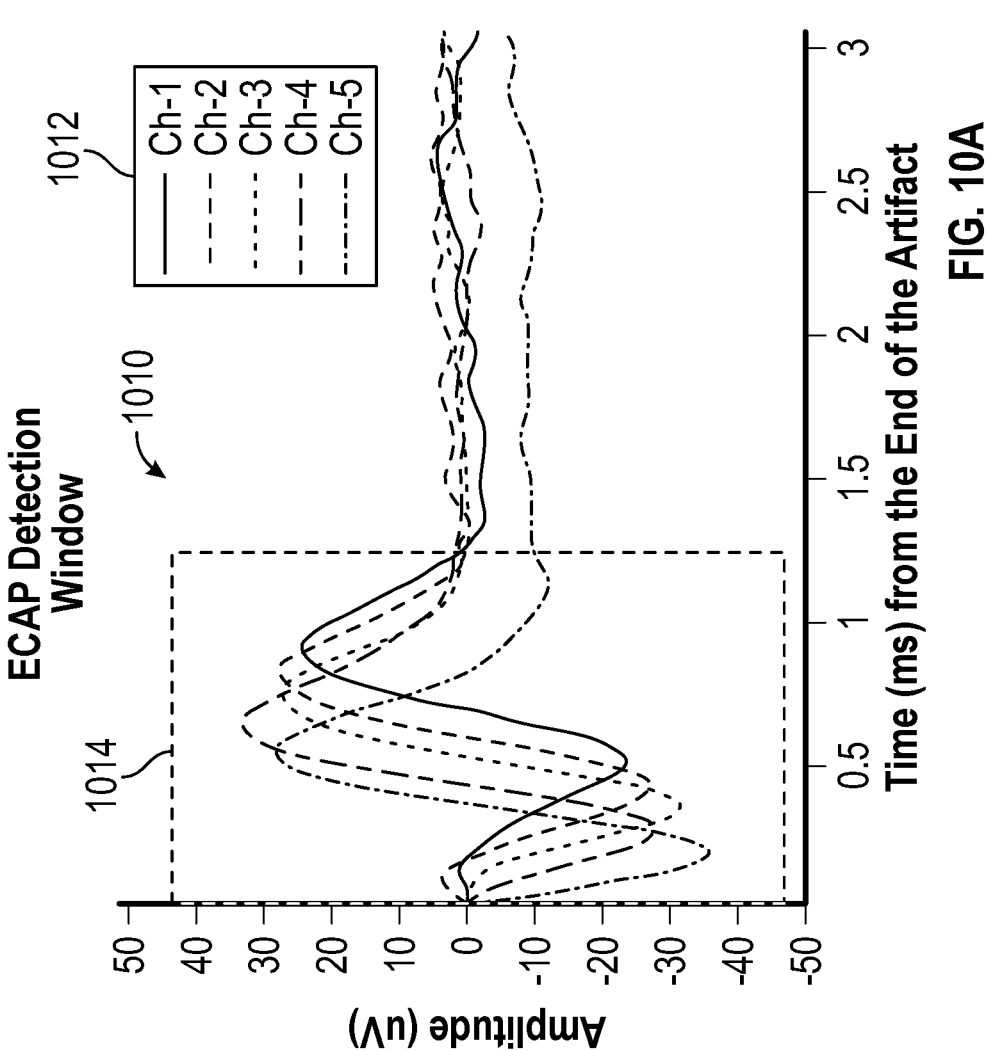
1012
Ch-1
Ch-2
Ch-3
Ch-4
Ch-5
ECAP Detection Window
1010
1014
Time (ms) from the End of the Artifact
Amplitude (uV)
FIG. 10A

Differential Channel 5-3

Time (ms) from the End of the Artifact

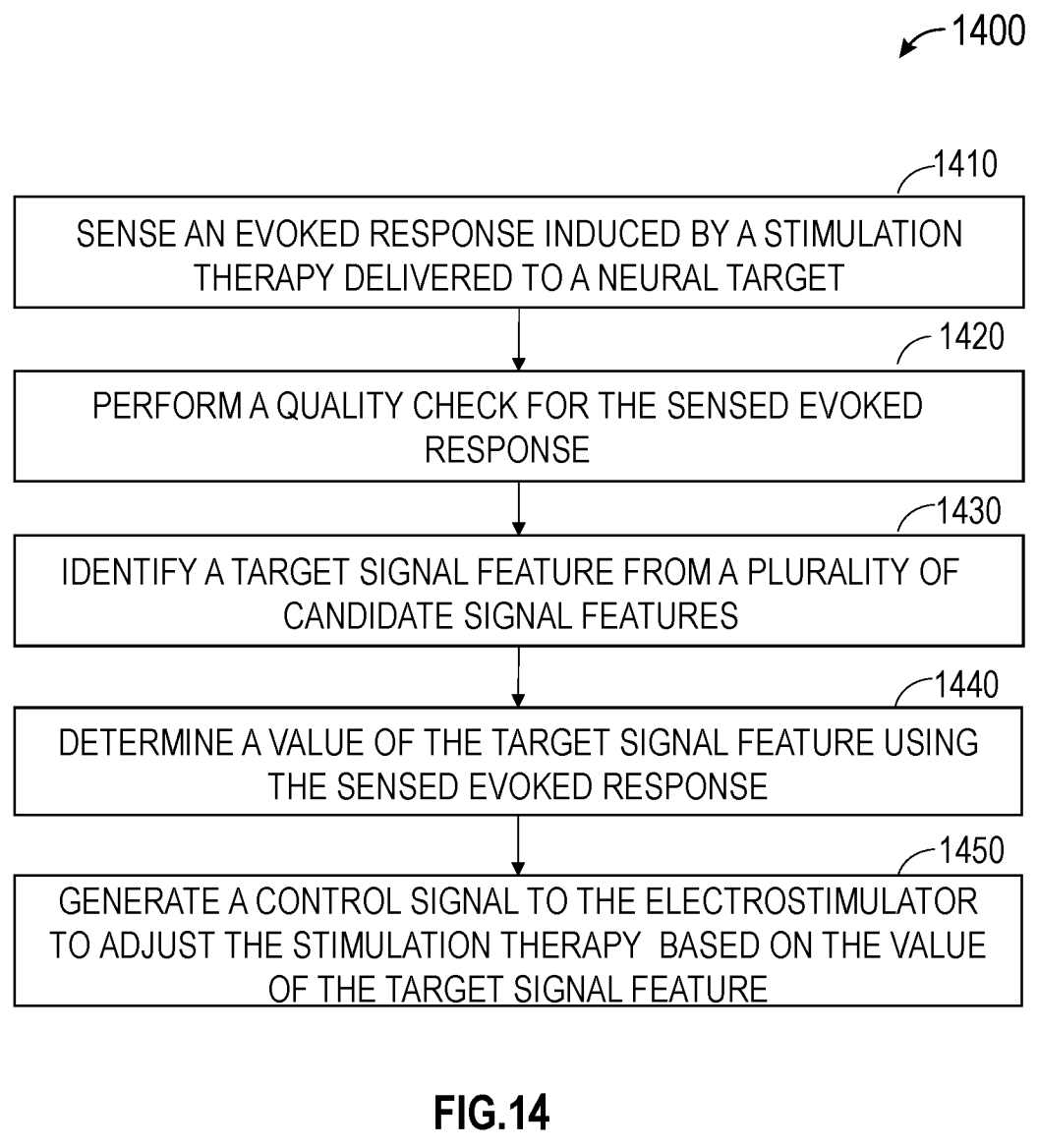

1400

1410

SENSE AN EVOKED RESPONSE INDUCED BY A STIMULATION THERAPY DELIVERED TO A NEURAL TARGET

1420

PERFORM A QUALITY CHECK FOR THE SENSED EVOKED RESPONSE

1430

IDENTIFY A TARGET SIGNAL FEATURE FROM A PLURALITY OF CANDIDATE SIGNAL FEATURES

1440

DETERMINE A VALUE OF THE TARGET SIGNAL FEATURE USING THE SENSED EVOKED RESPONSE

1450

GENERATE A CONTROL SIGNAL TO THE ELECTROSTIMULATOR TO ADJUST THE STIMULATION THERAPY BASED ON THE VALUE OF THE TARGET SIGNAL FEATURE

FIG.14

FEATURE SELECTION AND SENSING OPTIMIZATION FOR ADAPTIVE NEUROMODULATION THERAPY

CLAIM OF PRIORITY

This application claims the benefit of U.S. Provisional Application No. 63/398,284, filed on Aug. 16, 2022, which is hereby incorporated by reference in its entirety.

TECHNICAL FIELD

This document relates generally to medical devices, and more particularly, to adaptive neurostimulation based on signal features derived from evoked neural responses in a patient.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS systems have been used as a therapeutic modality for the treatment of chronic pain syndromes. PNS has been used to treat chronic pain syndrome and incontinence, with a number of other applications under investigation. FES systems have been applied to restore some functionality to paralyzed extremities in spinal cord injury patients. DBS can be used to treat a variety of diseases or disorders.

Stimulation systems, such as implantable electrostimulators, have been developed to provide therapy for a variety of treatments. An implantable electrostimulator can include a pulse generator and one or more leads each including a plurality of stimulation electrodes. The stimulation electrodes are in contact with or near target tissue to be stimulated, such as nerves, muscles, or other tissue. The control module generates a control signal to the pulse generator, which generates electrostimulation pulses that are delivered by the electrodes to the target tissue in accordance with an electrode configuration and a set of stimulation parameters.

Paresthesia-based spinal cord stimulation (SCS) has been used to treat chronic pain. Paresthesia is a sensation such as tingling, prickling, heat, cold, etc. that can accompany SCS therapy. Alternatively, SCS may be delivered with reduced strength below a paresthesia threshold to avoid inducing paresthesia, yet still achieve analgesia effect and clinically effective pain relief. Such paresthesia-free SCS, also known as sub-perception SCS, generally uses stimulation pulses at higher frequencies to achieve the paresthesia-free effect, which may consume more power than paresthesia-based SCS.

SUMMARY

In patients treated with paresthesia-based SCS, analgesia is usually observed within minutes. Conventional paresthesia-free or sub-perception SCS, however, generally has prolonged wash-in time, and it can take several hours to days until maximum or therapeutically effective analgesia effect can be achieved. As such, patients treated with conventional sub-perception therapies do not typically receive pain relief during their programming visit, and the effectiveness of the treatment cannot be immediately assured. Additionally, conventional sub-perception neurostimulation (e.g., SCS) uses higher-frequency pulses, which consumes more power and can drain the battery of an implantable pulse generator (IPG) more quickly and shortens the battery life. Moreover, therapy optimization can be a complex and onerous process for the conventional sub-perception SCS.

An improved sub-perception SCS, referred to as Fast-Acting Sub-Perception Therapy (FAST), has emerged as a highly effective and energy-efficient solution for sub-perception SCS, and can significantly reduce the wash-in time. The FAST methodology utilizes a stimulation frequency at a level below 100 Hz (or in some instances lower than 10 Hz) and a biphasic-symmetric waveform comprising an active charge phase followed by an active charge recovery phase (also referred to as a recharge phase). Compared to conventional sub-perception SCS therapies, FAST can achieve fast-acting analgesia, and significant and long-lasting pain relief (about six months after being activated in an example).

Sub-perception SCS (such as FAST) may be used to activate various neural targets including, for example, dorsal columns. The sub-perception nature of FAST implies that the necessary nerve activation (e.g., evoked neural activities capable of achieving the desired therapeutic effect) can be small and potentially below levels needed for an evoked potential. It can be technically challenging to detect small-amplitude evoked neural activities induced by sub-perceptions SCS such as FAST effectively and reliably. On the other hand, evoked neural activities have been used to evaluate therapy effectiveness or used in closed-loop control of neuromodulation therapy (also referred to as adaptive neurostimulation), where one or more signal features extracted from the evoked neural activities can be used as feedback in the closed-loop control of neuromodulation therapy. It is generally required that such signal features be capable of reliably distinguishing between different therapy states, such as between an optimal therapy state (e.g., therapeutic effect achieved without causing discomfort) and a sub-optimal, detrimental, or avoidance state (e.g., discomfort or other side effects in the patient). Conventional feature extraction from the evoked responses is largely based on heuristics or visual inspection. Without further selection or refinement, such feature extraction methods, when applied to respective evoked responses under different therapy states, may introduce significant overlap between respective feature values or value ranges and thus an inferior discriminatory performance in distinguishing between different therapy states such as an optimal therapy state and an avoidance state. The heuristics or visual inspection-based feature extraction can also be time and labor intensive, possibly error-prone, lack of reproducibility, and highly variable among inspectors with different levels of skills and experiences. For at least these reasons, the present inventors have recognized an unmet need for apparatus and methods for detecting small-amplitude evoked neural signals effectively and reliably, optimizing feature selection and extraction from the evoked neural signals, and using the extracted feature in a close-loop feedback control of neurostimulation therapy for treating or alleviating various neurological or autonomic disorders or other physiological conditions.

Various examples discussed in this document may improve the technology or technical field of device-based closed-loop neurostimulation, such as implantable devices for sub-perception SCS for controlling chronic pain. In accordance with various examples described herein, systems and methods are provided to detect evoked neural activities characterized by small amplitude or signal power, select a target "optimal" signal feature from a number of candidate signal features, and evaluate the optimal signal feature from the detected evoked neural activities. A training module of the system can determine optimal settings for sensing evoked response and for processing the evoked response, and the optimal signal that satisfies discriminatory criteria to distinguish between a first stimulation effect according to a first stimulation setting from a second stimulation effect according to a different second stimulation setting. Based on the optimal signal feature, the system may apply a feedback-control mechanism to automatically titrate electrostimulation therapy, such as by adjusting one or more waveform dosing parameters. With the closed-loop control of the electrostimulation therapy as discussed in this document, more reliable paresthesia-free effects and improved patient outcome can be achieved without comprising the therapeutic effects of sub-perception electrostimulation, the power consumption can be reduced and device battery life can be extended, and an overall system cost savings may be realized.

Example 1 is a system for providing electrostimulation to a patient, the system comprising: an electrostimulator configured to generate and deliver a stimulation therapy to a neural target of the patient; a sensor circuit configured to sense an evoked response induced by the stimulation therapy delivered to the neural target; and a controller circuit configured to: identify, from a plurality of candidate signal features, a target signal feature that satisfies a performance criterion for distinguishing (i) a first stimulation effect according to a first stimulation setting from (ii) a second stimulation effect according to a different second stimulation setting; determine from the sensed evoked response a value of the target signal feature; and generate a control signal to the electrostimulator to adjust the stimulation therapy based on the value of the target signal feature.

In Example 2, the subject matter of Example 1 optionally includes, wherein to identify the target signal feature that satisfies the performance criterion, the controller circuit is configured to: for each of the plurality of candidate signal features, determine a set of feature values from a set of evoked response signals, and evaluate a discrimination metric using the set of feature values, the discrimination metric measuring a performance of a candidate signal feature in distinguishing the first stimulation effect according to the first stimulation setting from the second stimulation effect according to the different second stimulation setting; and identify, from the plurality of candidate signal features, the target signal feature with a corresponding evaluated discrimination metric satisfying a specific condition.

In Example 3, the subject matter of any one or more of Examples 1-2 optionally include, wherein: the first stimulation setting includes a first threshold stimulation intensity for inducing patient comfort; and the second stimulation setting includes a second threshold stimulation intensity for inducing patient discomfort.

In Example 4, the subject matter of any one or more of Examples 1-3 optionally include, wherein the plurality of candidate signal features of an evoked response signal include one or more of: a signal amplitude range of within a specified time window; a signal curve length representing accumulated signal amplitude differences over consecutive unit times within the specified time window; or a signal power within a specified time window.

In Example 5, the subject matter of any one or more of Examples 2-4 optionally include, wherein the first stimulation effect includes a first statistical distribution of the set of feature values in response to the stimulation therapy according to the first stimulation setting, and the second stimulation effect includes a second statistical distribution of the set of feature values in response to the stimulation therapy according to the second stimulation setting, wherein, to evaluate the discrimination metric for each of the plurality of candidate signal features, the controller circuit is configured to determine a degree of overlap between the first statistical distribution and the second statistical distribution.

In Example 6, the subject matter of Example 5 optionally includes, wherein the discrimination metric includes a Fischer's Linear Discriminant (FLD) between the first statistical distribution and the second statistical distribution, wherein the controller circuit is configured to identify the target signal feature with a corresponding FLD value exceeding a threshold or being greater than FLD values of other of the plurality of candidate signal features.

In Example 7, the subject matter of any one or more of Examples 5-6 optionally include, wherein the discrimination metric includes a Jensen Shannon Divergence (JSD) metric between the first statistical distribution and the second statistical distribution, wherein the controller circuit is configured to identify the target signal feature with a corresponding JSD value exceeding a threshold or being greater than JSD values of other of the plurality of candidate signal features.

In Example 8, the subject matter of any one or more of Examples 1-7 optionally include, wherein the controller circuit is further configured to: identify a target sensing configuration from the plurality of candidate sensing configurations, including: determine a set of values of a specific signal feature from evoked responses sensed under each of a plurality of candidate sensing configurations; for each of the plurality of candidate sensing configurations, evaluate a discrimination metric using the set of values of the specific signal feature, the discrimination metric measuring a performance of the specific signal feature in distinguishing the first stimulation effect according to the first stimulation setting from the second stimulation effect according to the different second stimulation setting; and identify the target sensing configuration with a corresponding evaluated discrimination metric satisfying a specific condition; and determine the value of the target signal feature using an evoked response sensed in accordance with the target sensing configuration.

In Example 9, the subject matter of any one or more of Examples 1-8 optionally include, wherein the controller circuit is configured to: identify a target signal pre-processing setting from a plurality of candidate signal pre-processing settings, including: determine a set of values of a specific signal feature from evoked responses pre-processed using each of a plurality of candidate signal pre-processing settings; for each of the plurality of candidate signal pre-processing settings, evaluate a discrimination metric using the set of values of the specific signal feature, the discrimination metric measuring a performance of the specific signal feature in distinguishing the first stimulation effect according to the first stimulation setting from the second stimulation effect according to the different second stimulation setting; and identify the target signal pre-processing setting with a corresponding evaluated discrimination metric satisfying a specific condition; and determine the value of the target signal feature using an evoked response pre-processed using the target signal pre-processing setting.

In Example 10, the subject matter of Example 9 optionally includes, wherein the plurality of candidate signal pre-processing settings include: a plurality of signal filtering settings; a plurality of epoch averaging settings; or a plurality of feature window settings.

In Example 11, the subject matter of any one or more of Examples 1-10 optionally include, wherein the controller circuit is configured to identify the signal feature further based on response time or computation complexity or power consumption.

In Example 12, the subject matter of any one or more of Examples 1-11 optionally include, wherein the controller circuit is further configured to: perform a quality check on the sensed evoked response; and determine the value of the target signal feature using the sensed evoked response when the sensed evoked response passes the quality check.

In Example 13, the subject matter of Example 12 optionally includes, wherein to perform the quality check, the controller circuit is configured to: determine a congruency indicator between (i) a first value of a signal characteristic measured from the evoked response using a first algorithm and (ii) a second value of the signal characteristic measured from the evoked response using a second algorithm different than the first algorithm; and determine whether the sensed evoked response has passed the quality check based on the congruency indicator.

In Example 14, the subject matter of any one or more of Examples 12-13 optionally include, wherein to perform the quality check, the controller circuit is configured to: determine a cross-correlation between evoked responses sensed respectively from at least two different spatial locations with respect to the neural target; and determine whether the sensed evoked response has passed the quality check based on the cross-correlation.

In Example 15, the subject matter of Example 14 optionally includes, wherein the evoked responses are sensed respectively from at least three different spatial locations with respect to the neural target, wherein to perform the quality check, the controller circuit is configured to: for each of a number of pairs of the evoked response, determine a cross-correlation therebetween and an inter-response latency using the cross-correlation; and determine whether the sensed evoked response has passed the quality check based on the inter-response latencies corresponding to the number of pairs of the evoked responses.

Example 16 is a method for providing electrostimulation to a patient, the method comprising: sensing, via a sensor circuit, an evoked response induced by a stimulation therapy delivered to a neural target of the patient using an electro-stimulator; identifying, via a controller circuit, a target signal feature from a plurality of candidate signal features, the target signal feature satisfying a performance criterion for distinguishing (i) a first stimulation effect according to a first stimulation setting from (ii) a second stimulation effect according to a different second stimulation setting; determining from the sensed evoked response a value of the target signal feature; and generating, via the controller circuit, a control signal to the electrostimulator to adjust the stimulation therapy based on the value of the target signal feature.

In Example 17, the subject matter of Example 16 optionally includes, wherein identifying the target signal feature that satisfies the performance criterion includes: for each of the plurality of candidate signal features, determining a set of feature values from a set of evoked response signals, and evaluating a discrimination metric using the set of feature values, the discrimination metric measuring a performance of a candidate signal feature in distinguishing the first stimulation effect according to the first stimulation setting from the second stimulation effect according to the different second stimulation setting; and identifying, from the plurality of candidate signal features, the target signal feature with a corresponding evaluated discrimination metric satisfying a specific condition.

In Example 18, the subject matter of Example 17 optionally includes, wherein the first stimulation effect includes a first statistical distribution of the set of feature values in response to the stimulation therapy according to the first stimulation setting, and the second stimulation effect includes a second statistical distribution of the set of feature values in response to the stimulation therapy according to the second stimulation setting, wherein evaluating the discrimination metric for each of the plurality of candidate signal features includes determining a degree of overlap between the first statistical distribution and the second statistical distribution.

In Example 19, the subject matter of Example 18 optionally includes, wherein the discrimination metric includes a Fischer's Linear Discriminant (FLD) or a Jensen Shannon Divergence (JSD) between the first statistical distribution and the second statistical distribution, and the target signal feature is identified to have a corresponding FLD value or a JSD value exceeding a threshold or being greater than FLD values or JSD values of other of the plurality of candidate signal features.

In Example 20, the subject matter of any one or more of Examples 16-19 optionally include, further comprising: determining a set of values of a specific signal feature from evoked responses sensed under each of a plurality of candidate sensing configurations; for each of the plurality of candidate sensing configurations, evaluating a discrimination metric using the set of values of the specific signal feature, the discrimination metric measuring a performance of the specific signal feature in distinguishing the first stimulation effect according to the first stimulation setting from the second stimulation effect according to the different second stimulation setting; identifying, from the plurality of candidate sensing configurations, a target sensing configuration with a corresponding evaluated discrimination metric satisfying a specific condition; and determining the value of target signal feature using an evoked response sensed in accordance with the target sensing configuration.

In Example 21, the subject matter of any one or more of Examples 16-20 optionally include, further comprising: identifying a target signal pre-processing setting from a plurality of candidate signal pre-processing settings; and determining the value of the target signal feature using an evoked response pre-processed using the target signal pre-processing setting; wherein identifying the target signal pre-processing setting includes: determining a set of values of a specific signal feature from evoked responses pre-processed using each of the plurality of candidate signal pre-processing settings; for each of the plurality of candidate signal pre-processing settings, evaluating a discrimination metric using the set of values of the specific signal feature, the discrimination metric measuring a performance of the specific signal feature in distinguishing the first stimulation effect according to the first stimulation setting from the second stimulation effect according to the different second stimulation setting; and identifying, from the plurality of candidate signal pre-processing settings, the target signal pre-processing setting with a corresponding evaluated discrimination metric satisfying a specific condition.

In Example 22, the subject matter of any one or more of Examples 16-21 optionally include: performing, via the controller circuit, a quality check on the sensed evoked response, including: determining a congruency indicator between (i) a first value of a signal characteristic measured from the evoked response using a first algorithm and (ii) a second value of the signal characteristic measured from the evoked response using a second algorithm different than the first algorithm; and determining whether the sensed evoked response has passed the quality check based on the congruency indicator; and determining the value of the target signal feature using the sensed evoked response when the sensed evoked response passes the quality check.

In Example 23, the subject matter of any one or more of Examples 16-22 optionally include: performing, via the controller circuit, a quality check on the sensed evoked response, including: determining a cross-correlation between evoked responses sensed respectively from at least two different spatial locations with respect to the neural target; and determining whether the sensed evoked response has passed the quality check based on the cross-correlation; and determining the value of the target signal feature using the sensed evoked response when the sensed evoked response passes the quality check.

In this document, the "evoked neural activity" refers to neural activation elicited by stimulation pulses, such as an evoked potential or evoked compound action potential (ECAP). The evoked neural activity can be sensed from one or more neural structures or body parts from which neural responses (e.g., a bipotential signal) can be sensed and recorded. Although various examples described herein are specific to dorsal column evoked potentials, the evoked neural activity may correspond to other neural structures including, for example, peripheral nerves, dorsal roots, among other neural structures. In some examples, the evoked neural activity may include somatosensory evoked potentials (SSEP) recorded by electrodes placed on patient scalp over the sensory area of the brain in response to stimulation of specific nerves in, for example, ankle, wrist, or other external body parts.

The description that follows will generally focus on the use of the invention within a Spinal Cord Stimulation (SCS) systems. However, the present invention may find applicability with any implantable neurostimulator device system, including DBS system, Vagus Nerve Stimulation (VNS) system, Sacral Nerve Stimulation (SNS) systems, and the like. For example, apparatus and methods for detecting (and maintaining) exceptionally small evoked neural activities as described herein can be used to detect evoked neural activities in closed-loop DBS therapy, or therapies of other regions of the nervous system. The following examples illustrate various aspects of the examples described herein.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

FIG. 4 illustrates examples of various external devices capable of communicating with and programming stimulation in an IPG and ETS.

FIGS. 10A-10B illustrate an example of epoch-averaged ECAP signal segments from ECAP signals sensed from different sense channels, and inter-channel latencies derived from respective cross-correlations between pairs of the epoch-averaged ECAP signal segments.

FIG. 14 illustrates an example of a method for controlling an electrostimulation therapy delivered to a patient.

DETAILED DESCRIPTION

This document describes systems and methods for closed-loop control of electrostimulation based on signal features derived from evoked neural activities. An exemplary system comprises an electrostimulator to deliver a stimulation therapy to a neural target of a patient, a sensing circuit to sense an evoked response induced by the stimulation therapy, and a controller circuit to identify, from a plurality of candidate signal features, a target signal feature that satisfies a performance criterion for distinguishing a first stimulation effect according to a first stimulation setting from a second stimulation effect according to a different second stimulation setting. The target signal feature can be identified based on evaluations of a discrimination metric for each of the candidate signal features. The controller circuit can determine a value of the target signal feature from the sensed evoked response, and control the electrostimulator to adjust the stimulation therapy based on the value of the target signal feature.

Various examples described herein involve deep brain stimulation (DBS). The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

Figures 1, 2, 3:
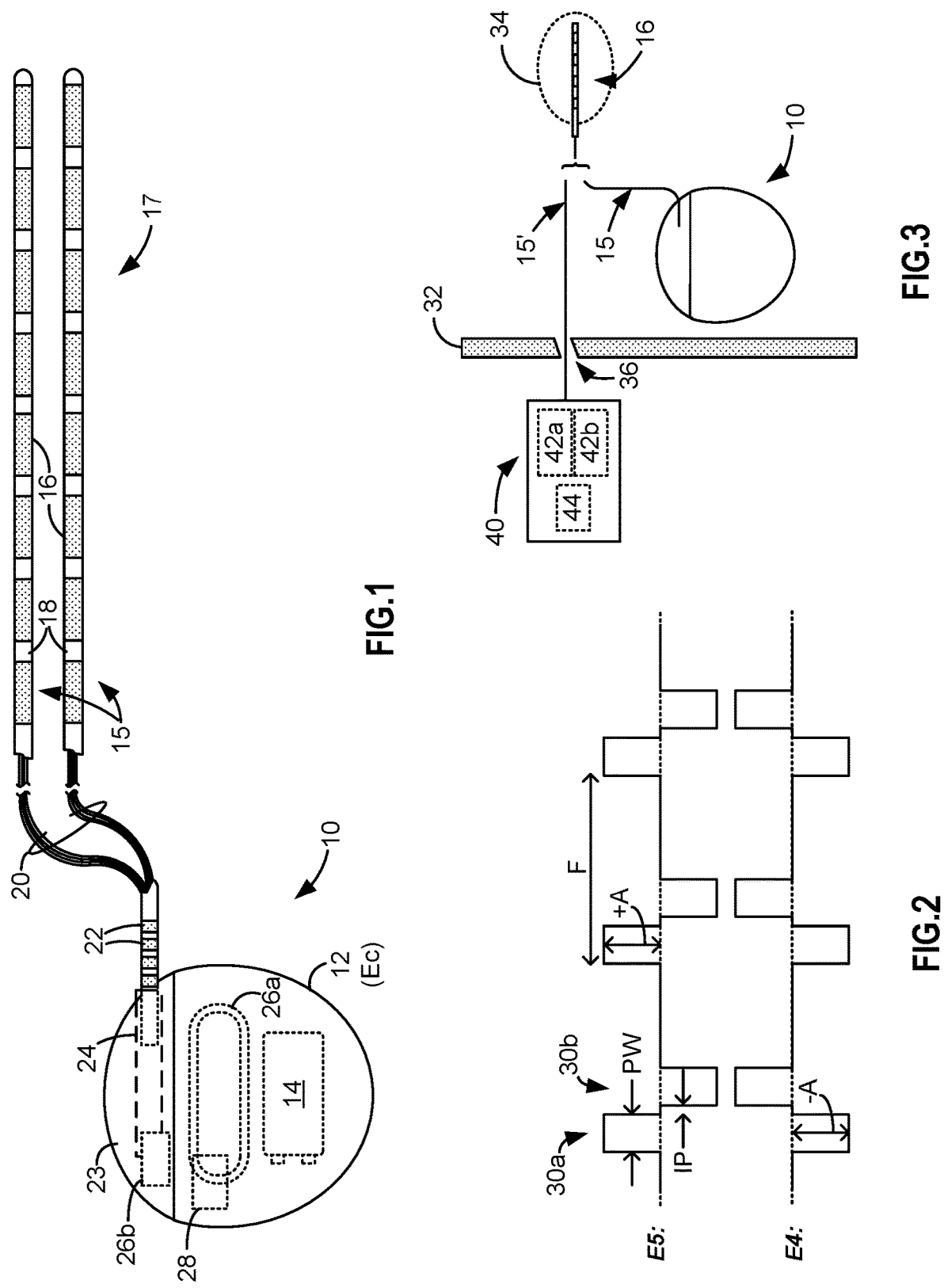
FIG. 1 illustrates an example of an Implantable Pulse Generator (IPG) useable for Spinal Cord Stimulation (SCS).
FIG. 2 illustrates an example of stimulation pulses producible by an IPG.
FIG. 3 illustrates an example of using an External Trial Stimulator (ETS) to provide stimulation before implantation of an IPG.

FIG. 1 illustrates, by way of example and not limitation, an Implantable Pulse Generator (IPG) 10 useable for Spinal Cord Stimulation (SCS). The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

By way of example and not limitation, in the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal contacts 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

The IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in the IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

FIG. 2 illustrates, by way of example and not limitation, an example of stimulation pulses producible by an IPG, such as the IPG 10. In this example, the electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripolar stimulation, quadripolar stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. In some examples, the second phase 30b may be charged balance with the first phase 30a if the integral of the amplitude and durations of the two phases are equal in magnitude. The width of each pulse, PW, is defined here as the duration of first pulse phase 30a, although pulse width could also refer to the total duration of the first and second pulse phases 30a and 30b as well. Note that an interphase period during which no stimulation is provided may be provided between the two phases 30a and 30b.

The IPG 10 includes stimulation circuitry 28 that can be programmed to produce the stimulation pulses at the electrodes as defined by the stimulation program. Stimulation circuitry 28 can for example comprise the circuitry described in U.S. Patent Application Publications 2018/0071513 and 2018/0071520, or in U.S. Pat. Nos. 8,606,362 and 8,620,436. The entirety of such references are incorporated herein by reference.

FIG. 3 illustrates, by way of example and not limitation, use of an External Trial Stimulator (ETS) 40 useable to provide stimulation, and at least a portion of external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 illustrates, by way of example and not limitation, a neuromodulation system 400 comprising various external devices capable of communicating with and programming stimulation in the IPG 10 and the ETS 40, including a patient, hand-held external controller 45, and a clinician programmer (CP) 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50.

In some examples, the external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

In some examples, the external controller 45 can have control circuitry 48 such as a microprocessor, microcomputer, an FPGA, other digital logic structures, etc., which is capable of executing instructions an electronic device. Control circuitry 48 can for example receive patient adjustments to stimulation parameters, and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

In an example where the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. The control circuitry 70 can execute the clinician programmer software 66 to generated a therapy plan and rendering the GUI 64. The therapy plan may include stimulation parameters chosen through the GUI 64 (e.g., electrode configurations and stimulation dosing parameters). The control circuitry 70 can enable communications via antennas 56a or 56b to communicate the therapy plan (e.g., stimulation parameters) to the patient's IPG 10. The IPG 10 may deliver electrostimulation in accordance with the therapy plan.

In an example, the therapy plan includes a sub-perception SCS plan comprising stimulation parameters with respective values set by the user via the GUI 64. In some examples, the sub-perception SCS can include a Fast-Acting Sub-Perception Therapy (FAST) program. The FAST program utilizes a stimulation frequency at a level below 100 Hz (or in some instances lower than 10 Hz) and a biphasic-symmetric pulse waveform comprising an active charge phase followed by an active recharge phase. Stimulation pulses in FAST can be defined by stimulation parameters such as stimulation amplitudes, pulse width, frequency, etc. In some examples, sub-perception SCS such as FAST can be delivered in discreet chunks, or boluses of stimulation pulses. In some examples, the sub-perception SCS plan may include device settings and parameters for sensing and processing evoked responses in response to a stimulation therapy, detecting evoked neural activities, extracting an optimal signal feature from the evoked neural activities that meets a predetermined performance criterion for distinguishing between different therapy states, and adjusting stimulation parameters so as to avoid or maintain a substantially low level of evoked neural activities while delivering the sub-perception SCS. Examples of a neuromodulation system for providing closed-loop neuromodulation therapy based on a selected signal feature satisfying the predetermined performance criterion are discussed below with reference to FIGS. 7-8.

Figure 5:
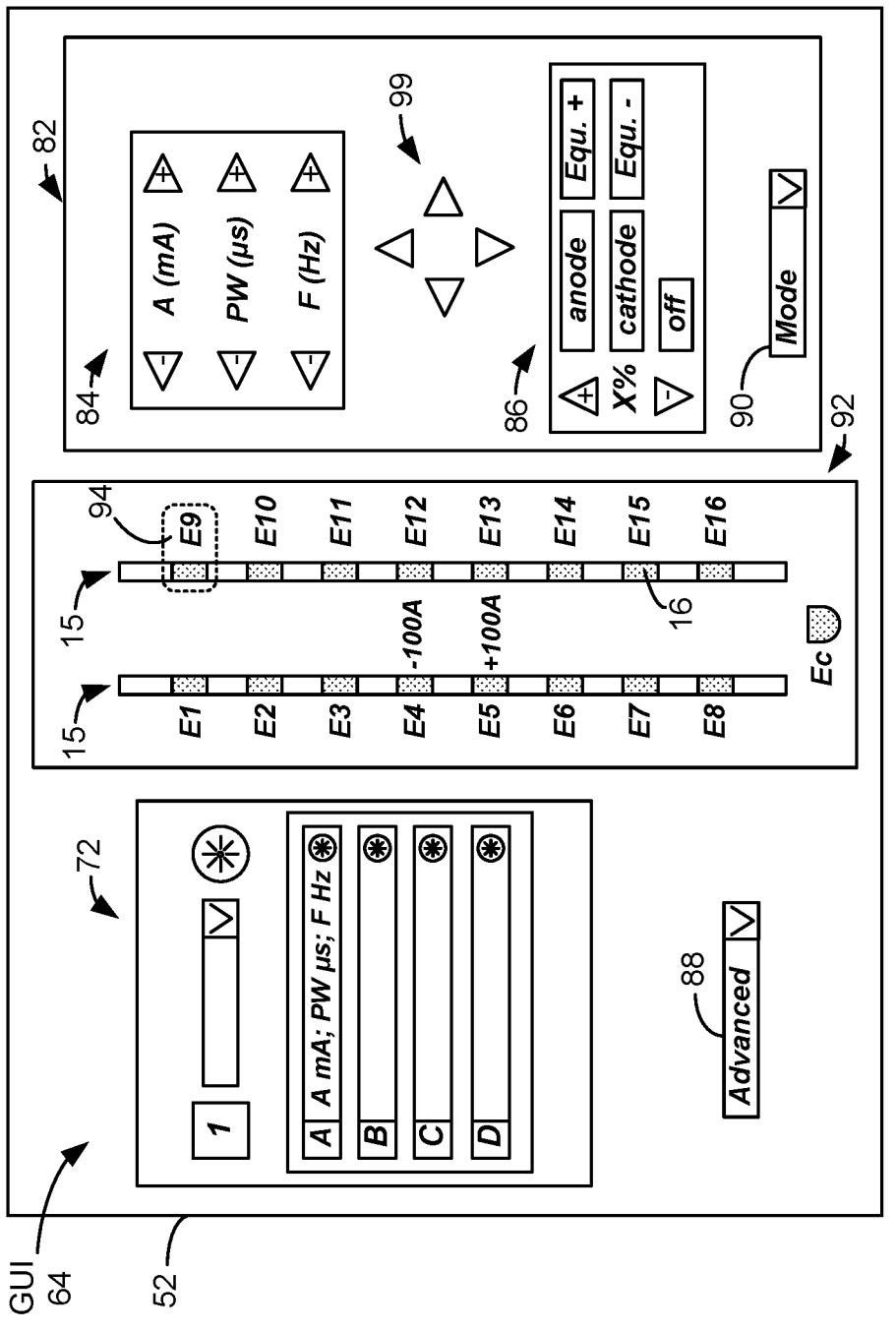
FIG. 5 illustrates an example of Graphical User Interface (GUI) for setting or adjusting stimulation parameters.

FIG. 5 illustrates, by way of example and not limitation, a portion of a GUI (such as one in a clinician programmer) for setting or adjusting stimulation parameters, such as the GUI 64 as shown in FIG. 4. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30*a*. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30*a* and 30*b* (e.g., each having a duration of PW, and with opposite polarities +A and −A). An advanced menu 88 can also be used (among other things) to define the relative durations and amplitudes of the pulse phases 30*a* and 30*b*, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion. While GUI 64 is shown as operating in the clinician programmer 50, the user interface of the external controller 45 may provide similar functionality.

Figure 6B:
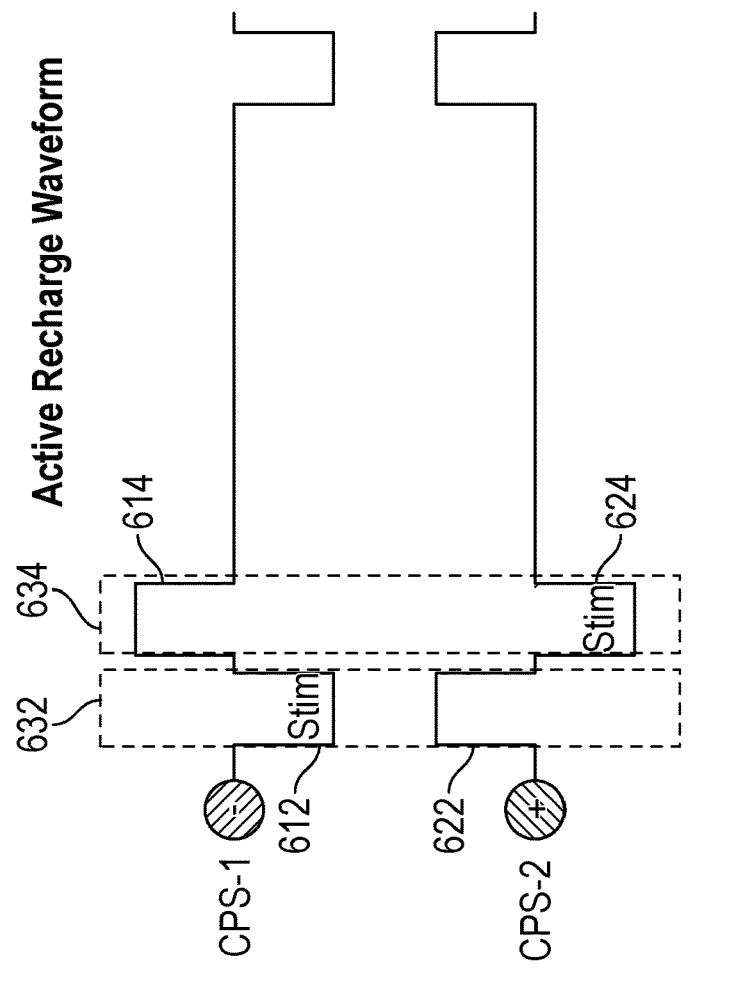
FIGS. 6A-6B illustrate example schematics of electrode configurations and stimulation waveforms that may be used in Fast-Acting Sub-Perception Therapy (FAST).
Figure 6A:
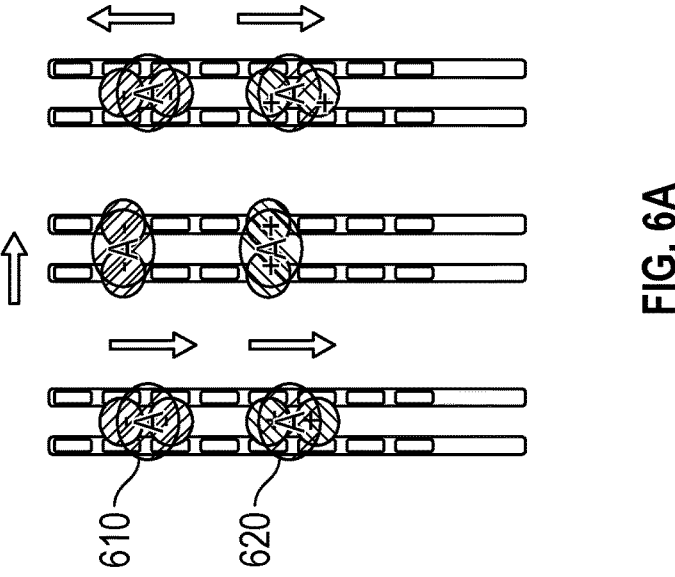

FIGS. 6A-6B illustrate, by way of example and not limitation, schematics of electrode configurations and stimulation waveforms that may be used in Fast-Acting Sub-Perception Therapy (FAST). The FAST can be programmed using a model-based steering algorithm that enables multiple central points of stimulation (CPS) to be moved rostrocaudally and mediolaterally simultaneously at a programmable step set by a user, as illustrated in FIG. 6A. In the illustrated example, by using symmetric biphasic waveforms, two separate CPSs can be implemented in the stimulation paradigm, including CPS-1 610 representing a virtual cathode, and CPS-2 620 representing a virtual anode. CPS-1 610 and CPS-2 620 can respectively sink or source various percentages of total current across multiple electrodes on the lead (also referred to as "current fractionalization"). For example, current applied to the virtual cathode CPS-1 610 can be fractionalized over a plurality of physical cathodes. Similarly, current applied to the virtual anode CPS-2 620 can be fractionalized over a plurality of physician anodes. The bipolar distance between the CPS-1 610 and CPS-2 620 can be programmed to be within a specified range, such as 10-14 mm. In an example, the bipolar distance is set to approximately 12 mm. The bipolar distance controls the spread of paresthesia during neural target search.

FIG. 6B illustrates biphasic symmetric waveforms of stimulation current for the virtual cathode CPS-1 610 and the virtual anode CPS-2 620. The biphasic symmetric waveform comprises a first charge phase 632, followed by a second active recharge (or charge recovery) phase 634. Current amplitude in each phase remains constant, thus a rectangular waveform. For each of the virtual cathode or the virtual anode, current amplitude of the charge phase 632 has the same magnitude but different sign (representing direction of current flow) than the current amplitude of the recharge phase 634. During the first charge phase 632, a negative current 612 (i.e., cathodic current) is injected through negatively configured contacts (physical cathodes corresponding to the virtual cathode CPS-1 610), and positive current 622 (i.e., anodic current) is injected through positively configured return contacts (physical anodes corresponding to the virtual anode CPS-2 620). During the second rectangular phase 634, the polarities of the virtual cathode CPS-1 and the virtual anode CPS-2 are reversed to achieve active charge balance: positive current 614 (i.e., anodic current) is applied to the assigned physical cathodes corresponding to virtual cathode CPS-1 610, and negative current 624 (i.e., cathodic current) is applied to the assigned physical anodes corresponding to virtual anode CPS-2 620.

Stimulation dosing parameters, such as amplitude, frequency (or stimulation rate), pulse width (PW), or waveform pattern of the stimulation waveform are programmable and can be set or adjusted by a user on a GUI. In an example, the frequency of the stimulation pulse (reciprocal of period) can be programmed to a value within a specific range, such as approximately 2-1200 Hz. In an example, the stimulation frequency can be programmed to 90 Hz. The pulse width (PW) can be programmed within a range, such as approximately $210\pm50$ micro-seconds ($\mu$s). To identify the electrode configuration and fine-tune the location of stimulation, a neural target search can be carried out using the CPS-1 and CPS-2 steered simultaneously in the rostro-caudal and medial-lateral dimensions at a programmable step (resolution) such as in approximately 300 $\mu$s increments. The stimulation amplitude can then be lowered to a programmable fraction of the perception threshold. Such a programming for FAST allows for a systematic optimization of the stimulating field that provides comprehensive overlap between the area of pain and paresthesia sensation.

Figure 7:
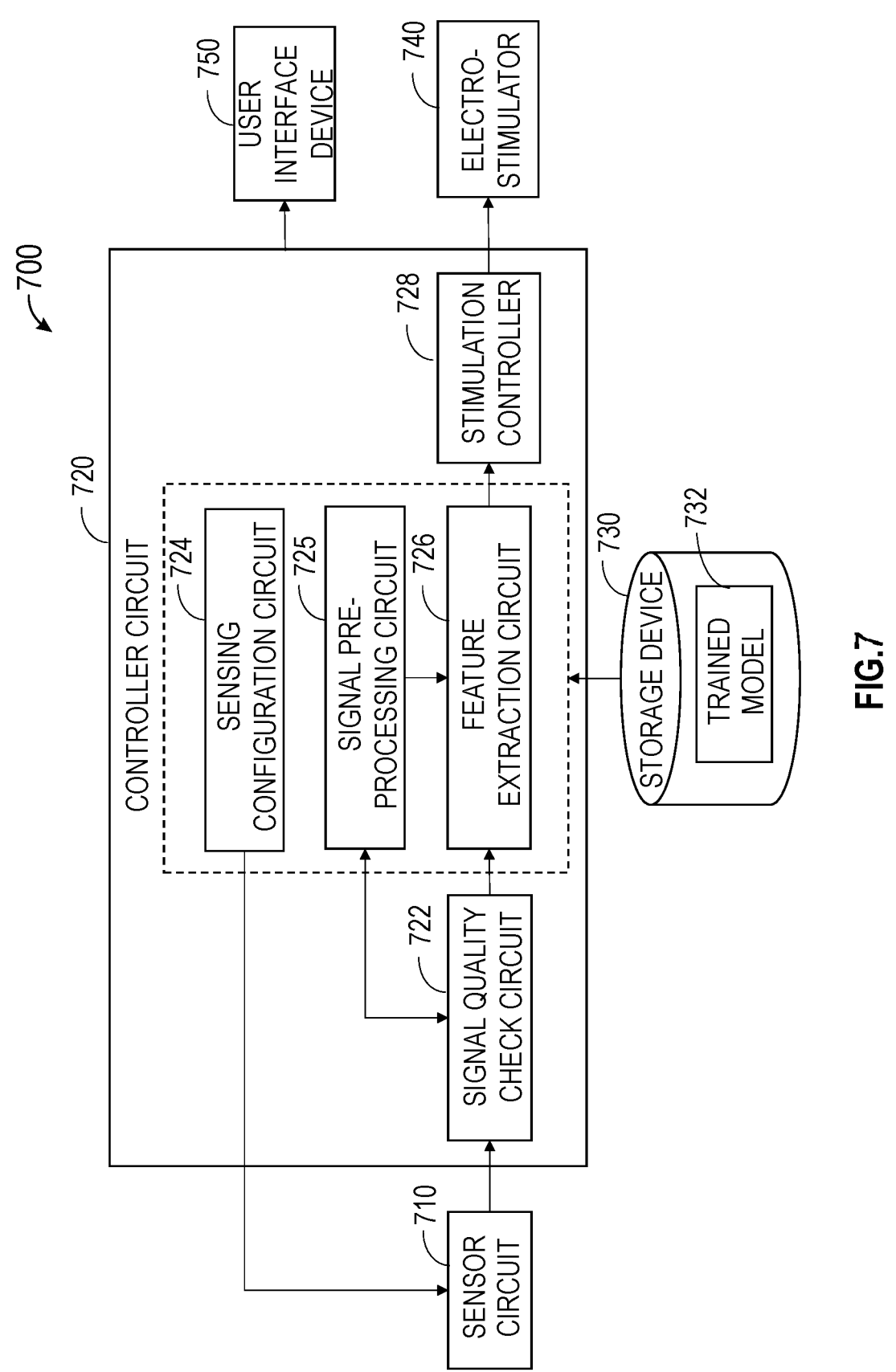
FIG. 7 illustrates an example of a neuromodulation system for providing closed-loop electrostimulation therapy to a patient.

FIG. 7 illustrates, by way of example and not limitation, a neuromodulation system 700 for providing closed-loop electrostimulation therapy to a patient. The neuromodulation system 700 can be configured to provide closed-loop neurostimulation to a neural target of the patient based on a signal feature derived from evoked neural activities. The signal feature can be selected from a plurality of candidate signal features and meets a performance criterion for distinguishing between a first therapy state (e.g., electrostimulation with therapeutic effect without causing discomfort) and a second therapy state (e.g., a sub-optimal, detrimental, or avoidance state where electrostimulation would cause patient discomfort or other side effects). The system 700 can provide closed-loop neurostimulation to treat or alleviate various neurological or autonomic disorders or other physiological condition. In an example, the system 700 can provide closed-loop spinal cord stimulation (SCS) for controlling chronic pain.

The neuromodulation system 700, which is an embodiment of the neuromodulation system 400, may include one or more of a sensor circuit 710, a controller circuit 720, a storage device 730, an electrostimulator 740, and at least one user interface device 750. Portions of the neuromodulation system 700 may be implemented in a stimulation device such as the IPG 10 or the ETS 40, or a controller device such as the RC 45 or the CP 50.

The sensor circuit 710 can be coupled to one or more sensors and configured to sense signals indicative of patient responses to electrostimulation of a neural target, such as SCS of a spinal neural target. The one or more sensors may be included in, or external to but communicatively coupled to, the IPG 10 or the ETS 40. In an example, the sensor circuit 710 can be coupled to one or more subcutaneous electrodes on one or more implantable leads, such as the electrodes 16 on one or more electrode leads 15, as illustrated in FIG. 1. The sensor circuit 710 can sense an evoked response induced by electrostimulation pulses produced by the electrostimulator 740 (e.g., included in the IPG 10) and delivered to the neural target via an electrode lead, such as one or more leads 15. The electrostimulation pulses may be generated and delivered to the neural target in accordance with one or more stimulation parameters. Examples of the stimulation parameters can include stimulation waveform dosing parameters such as amplitude (e.g., current amplitude), pulse width, pulse rate or frequency, pulse pattern, pulse waveform, among others. The stimulation parameters may also include electrode configurations that define polarities of the electrodes used for delivering stimulation and fractionalization of current or electrical energy among the electrodes. In some examples, a stimulation pulse train may be delivered in accordance with a pre-defined stimulation program, such as the Fast-Acting Sub-Perception Therapy (FAST) as described above with reference to FIGS. 6A-6B. The evoked response can be sensed from one or more of a dorsal column, a dorsal root, or a peripheral nerve. In some examples, the evoked responses can be somatosensory evoked potential (SSEP) signal recorded by electrodes placed on patient scalp over the sensory area of the brain in response to stimulation of specific nerves in, for example, ankle, wrist, or other external body parts. In an example, a biopotential signal can be sensed by one or more subcutaneous electrodes. The biopotential signal can include an evoked potential or evoked compound action potential (ECAP). The evoked responses (corresponding to the stimulation pulses) can include a plurality of inter-pulse segments of a biopotential signal.

In some examples, the sensor circuit 710 may be coupled to one or more ambulatory sensors configured to sense, for example, cardiac, pulmonary, neural, biochemical, or other physiological signals. Some of these signals may reveal characteristic signal properties in response to an onset, intensity, severity, duration, or patterns of pain. Examples of sensor signals can include cardiac signals such as a heart rate signal, a pulse rate signal, a heart rate variability signal, electrocardiograph (ECG) or intracardiac electrogram, cardiovascular pressure signal, or heart sounds signal, among others. The second signal may additionally or alternatively include a galvanic skin response (GUR) signal, an electrodermal activity (EDA) signal, a skin temperature signal, an electromyogram (EMG) signal, an electroencephalogram (EEG) signal, a magnetoencephelogram (MEG) signal, a hemodynamic signal such as a blood flow signal, a blood pressure signal, a blood perfusion signal, a photoplethysmography (PPG) signal, or a saliva production signal indicating the change of amount of saliva production, among others.

The controller circuit 720, which is an example of the control circuitry 48 of the RC 45 or the control circuitry 70 of the CP 50, can determine an "optimal" or improved stimulation setting (as defined by a set of stimulation parameters with respectively optimized values). A stimulation setting is deemed "optimal" if the neurostimulation delivered in accordance therewith can produce a desired therapeutic outcome (e.g., adequate pain relief) without producing significant side effects (e.g., discomfort or other symptoms). The controller circuit 720 can include circuit sets comprising one or more other circuits or sub-circuits, such as a signal quality check circuit 722, a sensing configuration circuit 724, a signal pre-processing circuit 725, a feature extraction circuit 726, and a stimulation controller 728. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the controller circuit 720 may be implemented as a part of a microprocessor circuit. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the methods or techniques described herein.

The signal quality check circuit 722 can verify the quality of an evoked response signal, such as evoked potential or ECAPs sensed by the sensor circuit 710. One purpose of the quality check is to determine whether the sensed evoked response represents a physiological and propagating neural activity elicited by the neurostimulation (and detected by the sensor circuit 710), or is instead non-physiological in nature (e.g., noise) or non-propagating local activity. A physiological and propagating evoked neural activity is more likely to pass the quality check than a non-physiological (e.g., noise) or non-propagating activity. In an example, only the evoked response that passes the quality check are used for assessing neurostimulation therapy efficacy and/or for closed-loop control of neurostimulation therapy.

Figures 9A, 9B:
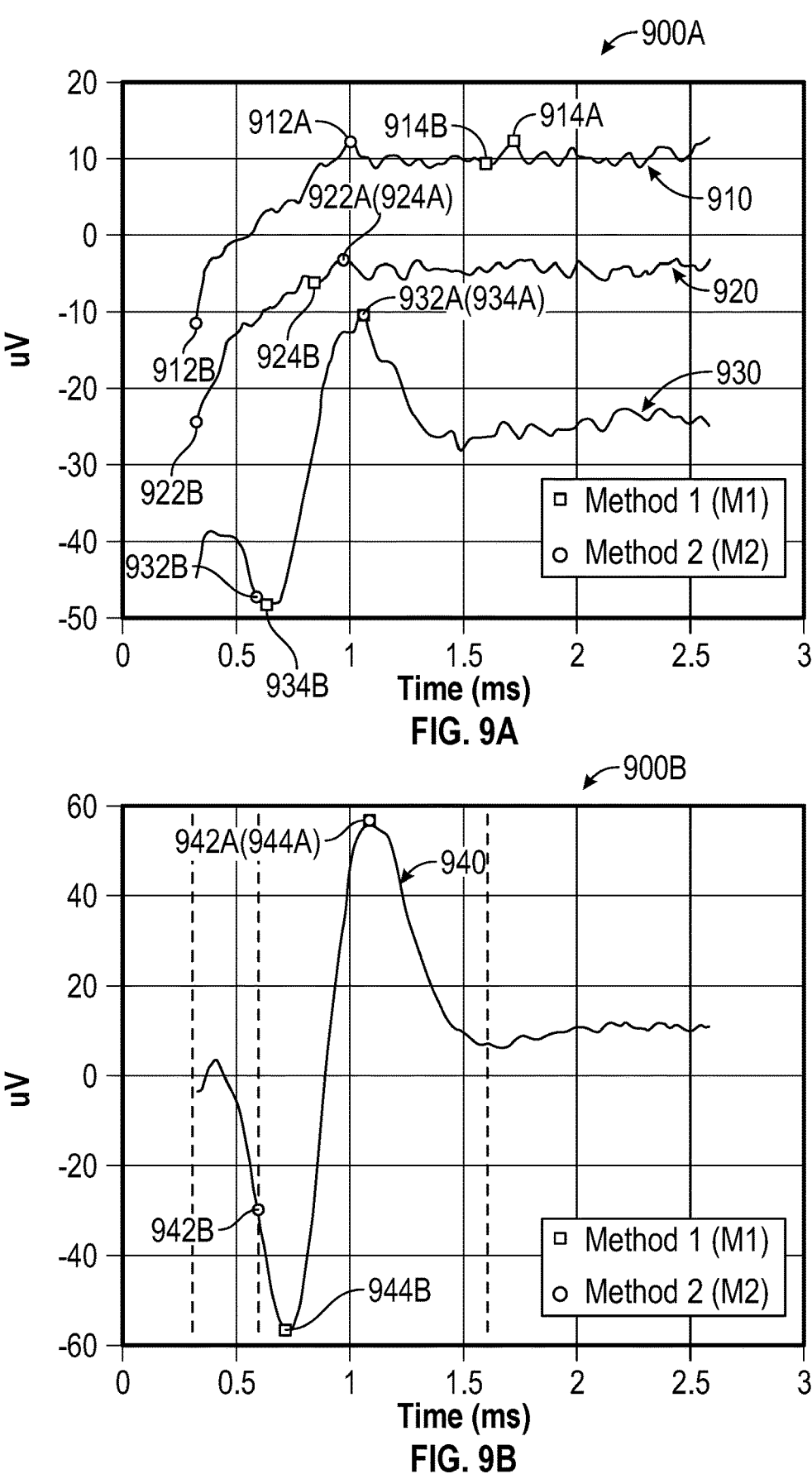
FIGS. 9A-9B illustrate an example of quality check of an evoked response signal using a cross-validation method.

In an example, the signal quality check circuit 722 can verify the quality of an evoked response signal using a cross-validation method, where some predetermined signal characteristics can be detected using a number of different algorithms from the same evoked response signal, and the quality of the evoked response signal can then be determined based on a congruency (or mismatch) between the signal characteristics respectively detected using different algorithms. Examples of such signal characteristics can include a signal peak value (e.g., a maximum value or a minimum value), peak timing (e.g., respective timings of the signal maximum or signal minimum), peak-to-peak value (e.g., a difference between a maximum value or a minimum value, also referred to as an amplitude range or a value range), peak-to-peak duration (e.g., duration between the signal maximum or signal minimum), a signal curve length representing accumulated signal amplitude differences over consecutive unit times (e.g., consecutive data sampling intervals), or a signal power (e.g., an area under the curve of the evoked response signal), within a specific time window. Referring to FIGS. 9A-9B, the diagrams 900A and 900B illustrate examples of validating the qualities of evoked response signals using the cross-validation method. In these examples, the evoked response signals are ECAP signal segments between two adjacent stimulation pulses. In some examples, the ECAP signal segments over a number of epochs can be averaged to produce an averaged ECAP signal segment. Neural activities may be detected from the ECAP signal segment (or the averaged ECAP signal segment) within a user-defined neural activity detection window ($W_{EP}$). Examples of averaged ECAP signal segments, the neural activity detection window ($W_{EP}$), and detecting neural activities from the ECAP signal segment are described in U.S. Patent Application No. 63/276,026, the entirety of which are incorporated herein by reference.

FIG. 9A illustrates, by way of example, three averaged ECAP signal segments 910, 920, and 930 derived from ECAP signals recorded when the patient is coughing. FIG. 9B illustrates an averaged ECAP signal segment 940 derived from a ECAP signal recorded when the patient is in a sitting position. Two distinct methods, M1 and M2, are independently applied to each of the averaged ECAP signal segments 910-940 to detect an "N1P2" waveform pattern, characterized by a first negative phase (N1) followed by a second positive phase (P2). Detecting an "N1P2" pattern includes detecting a negative peak (local minimum) and a positive peak (local maximum) within the neural activity detection window ($W_{EP}$).

In an illustrated example, the first N1P2 pattern detection method M1 is a min-max method, the second N1P2 pattern detection method is a hysteresis-based method. The min-max method looks at the minimum and maximum values within a given x-axis interval, and determines the minimum value as the "N1" phase and the maximum value as the "P2" phase. The hysteresis-based method takes into account the width of a peak and second or higher order derivatives in said peak to determine if it is a valid negative or positive signal peak ("N1" or "P2" phase) or just a noise spike. A congruency (or mismatch) between the N1P2 patterns detected respectively using methods M1 and M2 can be determined. In an example, the congruency (or mismatch) can be determined as a difference between the positive peak timings ($\Delta t_P = t_P(M1) - t_P(M2)$), a difference between negative peak timings ($\Delta t_N = t_N(M1) - t_N(M2)$), a difference between positive peak amplitudes ($\Delta X_P = X_P(M1) - X_P(M2)$), a difference between negative peak amplitudes ($\Delta X_N = X_N(M1) - X_N(M2)$), or a combination thereof. In an example, the signal quality check circuit 722 can calculate a mismatch score (S) using a weighted combination of the differences across a number of (e.g., N) signal characteristics:

$$S = w_1\Delta_1 + w_2\Delta_2 + \ldots + w_N\Delta_N \qquad (1)$$

where $\Delta_k$ (for k=1, 2, . . . , N) represents a difference in the k-th signal characteristic evaluated using methods M1 and M2 (such as one of $\Delta t_P$, $\Delta t_N$, $\Delta X_P$, or $\Delta X_N$), and $w_k$ represents an adjustable weight assigned to the k-th characteristic. The mismatch score (S) indicates how likely the evoked response is physiological and propagating neural activity (rather than noise). A smaller mismatch score (S) indicates a higher degree of congruency between the detections using distinct methods M1 and M2, and accordingly a higher likelihood that the ECAP signal segment represents physiological and propagating neural activity. In some examples, the signal quality check circuit 722 can compare the mismatch score (S) to one or more thresholds to determine the likelihood the evoked response represents physiological and propagating neural activity. For example, if S is less than a first (lower) threshold $S_{TH1}$ (that is, $S < S_{TH1}$), then a high likelihood is indicated; and the evoked response signal can be automatically passed on to the signal pre-processing circuit 725 and the feature extraction circuit 726 for assessing neurostimulation effects and for closed-loop control of neurostimulation therapy. If S is higher than a second threshold $S_{TH2}$ (higher than $S_{TH1}$) (that is, $S > S_{TH2}$), then a low likelihood is indicated; and the evoked response signal is deemed unreliable and will not be used for evaluating neurostimulation effects or for closed-loop control of neurostimulation therapy. If S takes a value between $S_{TH1}$ and $S_{TH2}$ (that is, $S_{TH1} < S < S_{TH2}$), then a marginal likelihood is indicated; and the evoked response signal will not be automatically used, but may be selected upon user request, for evaluating neurostimulation effects and for closed-loop control of neurostimulation therapy.

As illustrated in FIG. 9A, for ECAP signal segment 910, the positive peak 912A detected using M1 method is far off in timing (x-axis) from the positive peak 914A detected using M2 method, and the negative peak 912B detected using M1 method is far off in timing (x-axis) and in amplitude (y-axis) from the negative peak 914B detected using M2 method. The mismatch score (S), such as computed using Equation (1) above, exceeds the threshold $S_{TH2}$. As such, ECAP signal segment 910 is deemed not reliable as it is less likely a physiological and propagating neural activity. For ECAP signal segment 920, the positive peak 922A detected using M1 method overlaps with the positive peak 924A detected using M2 method; however, the negative peak 922B detected using M1 method is far off in timing (x-axis) and in amplitude (y-axis) from the negative peak 924B detected using M2 method. The mismatch score (S) exceeds the threshold $S_{TH2}$, such that ECAP signal segment 920 is deemed not reliable as it is less likely a physiological and propagating neural activity. For ECAP signal segment 930, the positive peak 932A detected using M1 method overlaps with the positive peak 934A detected using M2 method, and the negative peak 932B detected using M1 method is close enough in timing (x-axis) and in amplitude (y-axis) to the negative peak 934B detected using M2 method. The mismatch score (S) in this case is small enough to be less than $S_{TH1}$. The ECAP signal segment 930 is deemed reliable as it is more likely a physiological and propagating neural activity, and can be passed on to the signal pre-processing circuit 725 and the feature extraction circuit 726 for assessing neurostimulation effects and for closed-loop control of neurostimulation therapy.

For the ECAP signal segment 940 shown in FIG. 9B, the positive peak 942A detected using M1 method overlaps with the positive peak 944A detected using M2 method. The negative peak 942B detected using M1 method is close enough in timing (x-axis) to the negative peak 944B detected using M2 method, but differ significantly in amplitude (y-axis) than the negative peak 944B. The mismatch score (S), such as computed using Equation (1) above, is between $S_{TH1}$ and $S_{TH2}$ ($S_{TH1} < S < S_{TH2}$). The ECAP signal segment 940 is deemed marginally reliable, and can be selected for evaluating neurostimulation effects and for closed-loop control of neurostimulation therapy upon user request. In some examples, the user may adjust the weights $w_k$ (for k=1 to N) such that larger weights are assigned to timing difference $\Delta t_P$ and $\Delta t_N$, but smaller weights assigned to amplitude differences $\Delta X_P$ and $\Delta X_N$. With such weight assignment, the mismatch score (S) for ECAP signal segment 940 is less than $S_{TH1}$ ($S < S_{TH1}$); and the ECAP signal segment 940 can then be automatically selected for evaluating neurostimulation effects and for closed-loop control of neurostimulation therapy.

In addition or alternative to the cross-validation method as discussed above, the signal quality check circuit 722 may verify the quality of an evoked response signal (e.g., a ECAP signal) based on a cross-correlation ($R_{xy}$ ($\tau$)) between two evoked response signals x(t) and y(t) sensed respectively from two distinct spatial locations with respect to the neural target being stimulated. The cross-correlation $R_{xy}$ ($\tau$) measures a similarity between the two evoked response signals at different time lags ($\tau$) between the two signals. The signal quality check circuit 722 can determine that the sensed evoked response x(t) or y(t) has passed the quality check if the cross-correlation ($R_{xy}$ ($\tau$)) at a specified time lag η value (e.g., $\tau$=0, or other values) exceeds a threshold value.

In an example, the signal quality check circuit 722 can determine an inter-response latency (L) between two evoked response signals x(t) and y(t) from the cross-correlation ($R_{xy}$ ($\tau$)) therebetween. The inter-response latency (L) can be determined as the time lag ($\tau$) for which the cross-correlation reaches a maximum, that is, $L = \text{argmax}_\tau R_{xy}(\tau)$. As discussed above, the quality check of an evoked response signal is to determine whether the evoked response represents a physiological and propagating neural activity elicited by the neurostimulation pulses, or a non-physiological effect such as noise. For a physiological and propagating neural activity, a latency (time-lag) can be detected from evoked responses sensed at two distinct locations along the propagation pathway. Conversely, an absence of such detectable latency may indicate that the evoked response signal is non-physiological or non-propagating, or substantially interfered by non-neurophysiological signals (e.g., cardiac artifacts). In an example, the signal quality check circuit 722 may determine if a sensed signal has a consistent delay with respect to a fixed feature of another signal. For example, if a sensed signal resembles a local field potential (LFP) and consistently (e.g., over a specific time period during stimulation) exhibits a fluctuation or peak at a fixed distance from N1 in an evoked response signal (e.g., an ECAP signal), then although the LFP-like signal itself does not propagate, it may indicate a presence of an biophysical and propagating evoked response (e.g., ECAP).

Figure 10B:
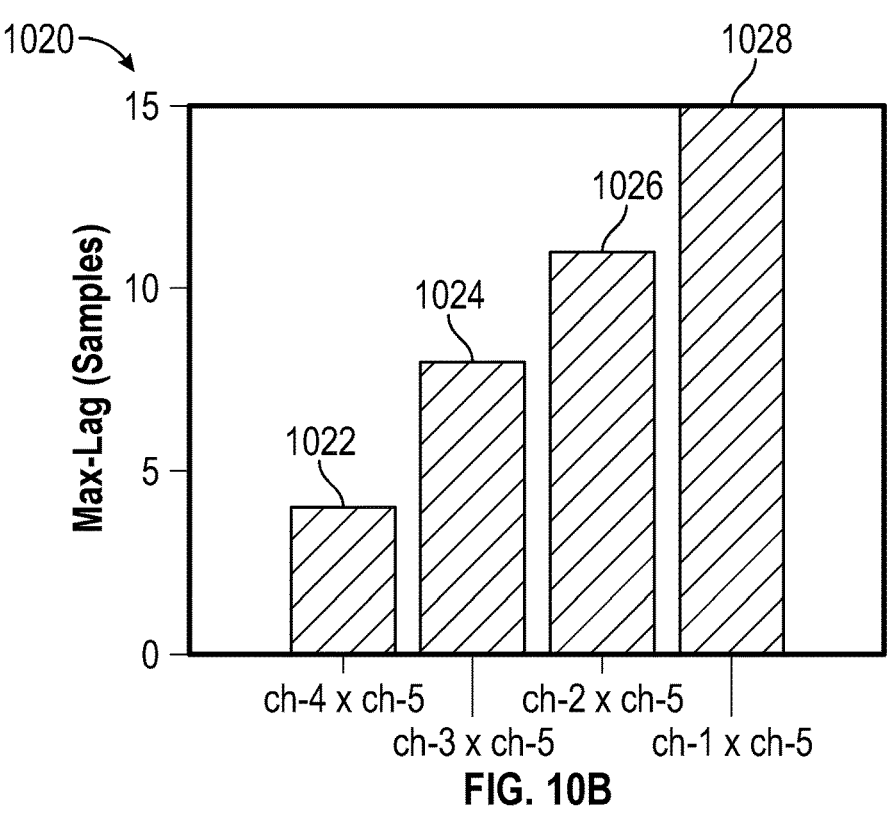

In an example, the sensor circuit 710 can sense a plurality of evoked responses respectively from at least three different spatial locations with respect to the neural target (e.g., at least three electrode configurations). The signal quality check circuit 722 can determine latencies from cross-correlations between pairs of the sensed plurality of evoked responses, and determine whether the sensed evoked response (e.g., x(t)) has passed the quality check based on a pattern of determined latencies. Referring to FIG. 10A, a diagram shows an overlay plot of epoch-averaged ECAP signal segments 1010 obtained from ECAP signals sensed from different sense channels 1012 (e.g., channels 1 through 5), where each channel is defined by a unique bipolar sensing configuration with an anode (S+) and a cathode (S−), as shown in table 1016. In an example, the anode (S+) and a cathode (S−) can be selected from the electrode array 17 on one of the electrode leads 15. For a given lead placement, different sensing configurations (S+ and S− combination) represent distinct spatial locations where the ECAP signals are sensed. FIG. 10B illustrates inter-channel latencies 1020 derived from respective cross-correlations between pairs of the epoch-averaged ECAP signal segments sensed from respective channels as shown in FIG. 10A. In some examples, the cross-correlations may be computed using respective portions of the epoch-averaged ECAP signal segments 1010 within a pre-determined or user-defined ECAP detection window 1014. The ECAP detection window 1014 may be set to begin after a stimulation artifact in the ECAP signal to avoid or reduce spurious effect introduced to the cross-correlation calculation. By way of example and not limitation, the inter-channel latencies in FIG. 10B include a latency 1022 ($L_{45}$) between ECAP signal segments of channels 4 and 5, a latency 1024 ($L_{35}$) between ECAP signal segments of channels 3 and 5, a latency 1026 ($L_{25}$) between ECAP signal segments of channels 2 and 5, and a latency 1028 ($L_{15}$) between ECAP signal segments of channels 1 and 5. In this example, an increasing trend of the inter-channel latencies ($L_{45}$<$L_{35}$<$L_{25}$<$L_{15}$) is consistent with spatial displacements (d) between the channels ($d_{45}$<$d_{35}$<$d_{25}$<$d_{15}$). Based on such inter-channel latency trend, the signal quality check circuit 722 can determine that the sensed evoked response (e.g., any of the ECAP signal segments of channels 1 through 5) has passed the quality check, and can automatically be selected for evaluating neurostimulation effects and for closed-loop control of neurostimulation therapy.

Figure 11A:
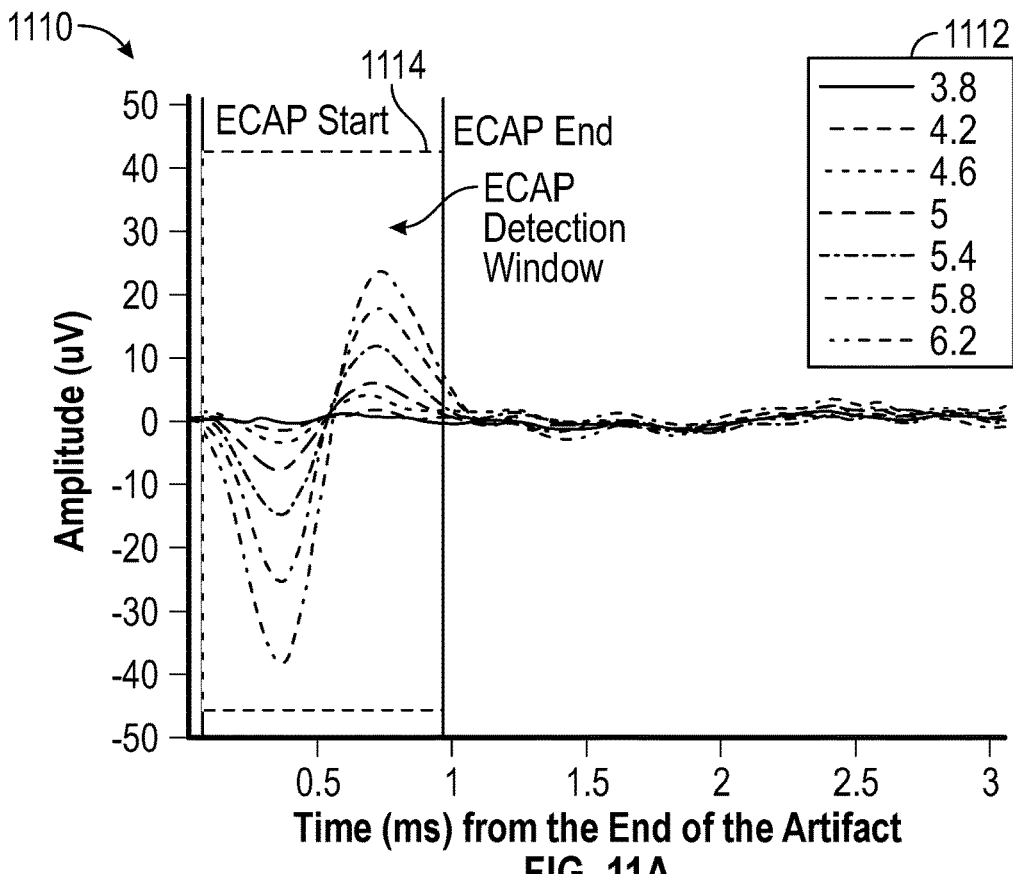
FIGS. 11A-11B illustrate an example of quality check of an evoked response signal based on patterns of inter-channel latencies under different stimulation current amplitudes.
Figure 11B:
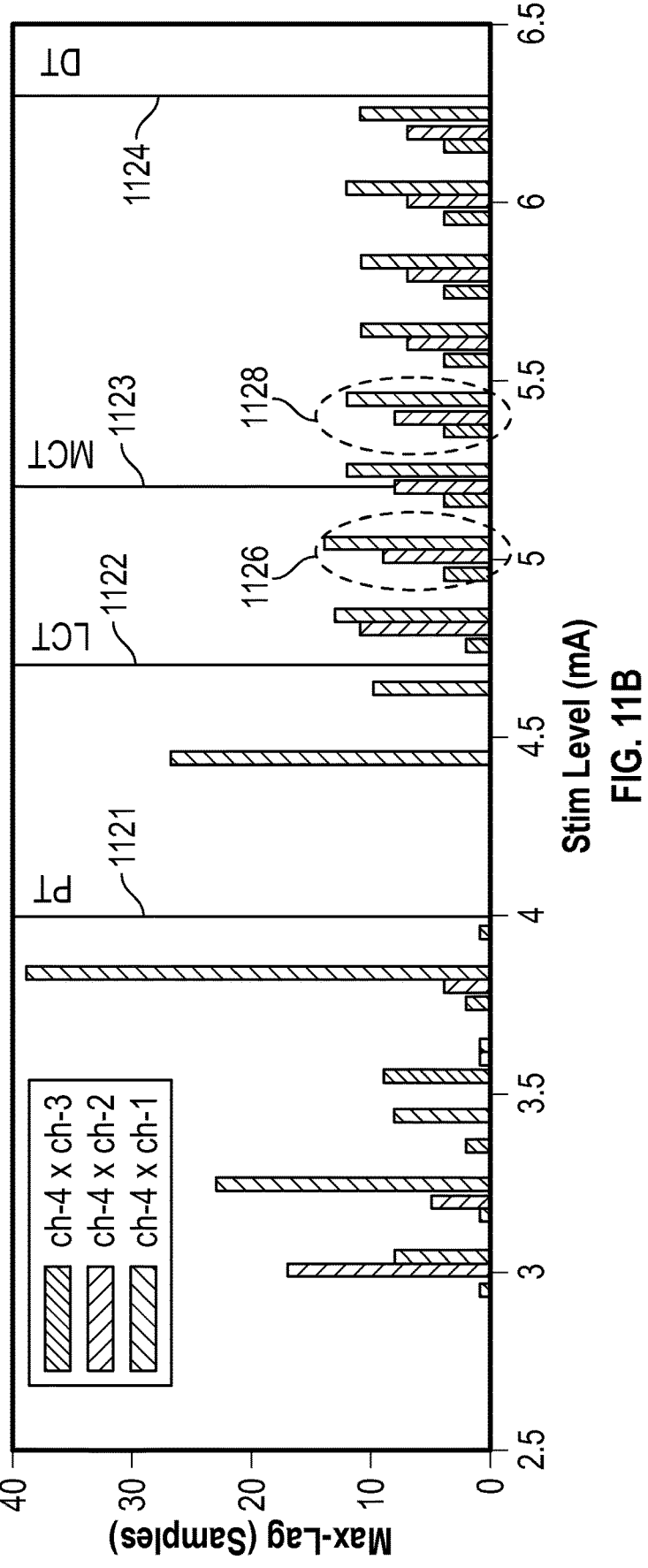

In some examples, evoked response signals can be sensed from two or more spatial locations (e.g., two or more different channels) in response to electrostimulation delivered in accordance with different stimulation settings (e.g., different stimulation current amplitudes above a particular threshold), and the inter-channel latencies can be evaluated under different stimulation settings. FIGS. 11A-11B and FIGS. 12A-12B illustrate examples of quality check of an evoked response signal based on patterns of inter-channel latencies under different stimulation current amplitudes. Specifically, FIG. 11A illustrates an example of epoch-averaged ECAP signal segments 1110 calculated using ECAP signals sensed from a patient via a sense channel. The ECAP signals were sensed in response to stimulation at a number of stimulation current amplitudes 1112. FIG. 11B illustrates inter-channel latencies under different stimulation current amplitudes. By way of example and not limitation, inter-channel latencies are evaluated between ECAP signal segments sensed from channels 4 and 3 ($L_{43}$), between ECAP signal segments sensed from channels 4 and 2 ($L_{42}$), and between ECAP signal segments sensed from channels 4 and 1 ($L_{41}$). The inter-channel latencies $L_{43}$, $L_{42}$, and $L_{41}$ are each derived from respective cross-correlations of the averaged ECAP signal segments within a pre-determined or user-defined ECAP detection window 1114, under different stimulation current amplitudes. The ECAP signal segments used for cross-correlation and the inter-channel latency calculation are similar to those shown in FIG. 11A. The signal quality check circuit 722 can determine whether the inter-channel latencies $L_{43}$, $L_{42}$, and $L_{41}$ form a particular pattern at a stimulation current amplitude above a particular threshold, such as a perception threshold (PT) 1121, a lowest comfortable threshold (LCT) 1122, a maximum comfortable threshold (MCT) 1123, or a discomfort threshold (DT) 1124, as illustrated in FIG. 11B. For example, at stimulation current amplitude I=5.0 mA (above the LCT but below the MCT), the inter-channel latencies 1126 form an increasing trend ($L_{43}$<$L_{42}$<$L_{41}$) consistent with spatial locations (or displacement) of the sensing channels 1 through 4 (spatial displacements $d_{43}$<$d_{42}$<$d_{41}$). Similarly, at stimulation current amplitude I=5.4 mA (above the MCT but below the DT), the inter-channel latencies 1128 form an increasing trend consistent with spatial locations (or displacement, d) of the sensing channels 1 through 4 (spatial displacements $d_{43}$<$d_{42}$<$d_{41}$). FIGS. 11A-11B also illustrated that as stimulation current amplitudes increases, while the ECAP signal amplitude increases (as shown in FIG. 11A), the ECAP inter-channel latency for a particular pair a channels (e.g., channels 4 and 1) remain unchanged mostly (e.g., similar $L_{41}$ values for stimulation current amplitudes of 5.0 mA and 5.4 mA), and the pattern of the inter-channel latencies across pairs of channels also remain unchanged mostly (e.g., similar patterns between inter-channel latencies 1126 and inter-channel latencies 1128). Such a consistent pattern of increasing inter-channel latencies across physically separated channels once the stimulation amplitude is above the threshold at which ECAPs first start appearing also signifies physiological and propagating neural activities elicited by the stimulation. Based on the presence of such inter-channel latency trend, the signal quality check circuit 722 can determine that, for certain stimulation current amplitudes, the sensed evoked response (e.g., any of the ECAP signal segments of channels 1 through 4) has passed the quality check, and can automatically be selected for evaluating neurostimulation effects and for closed-loop control of neurostimulation therapy.

Figure 12A:
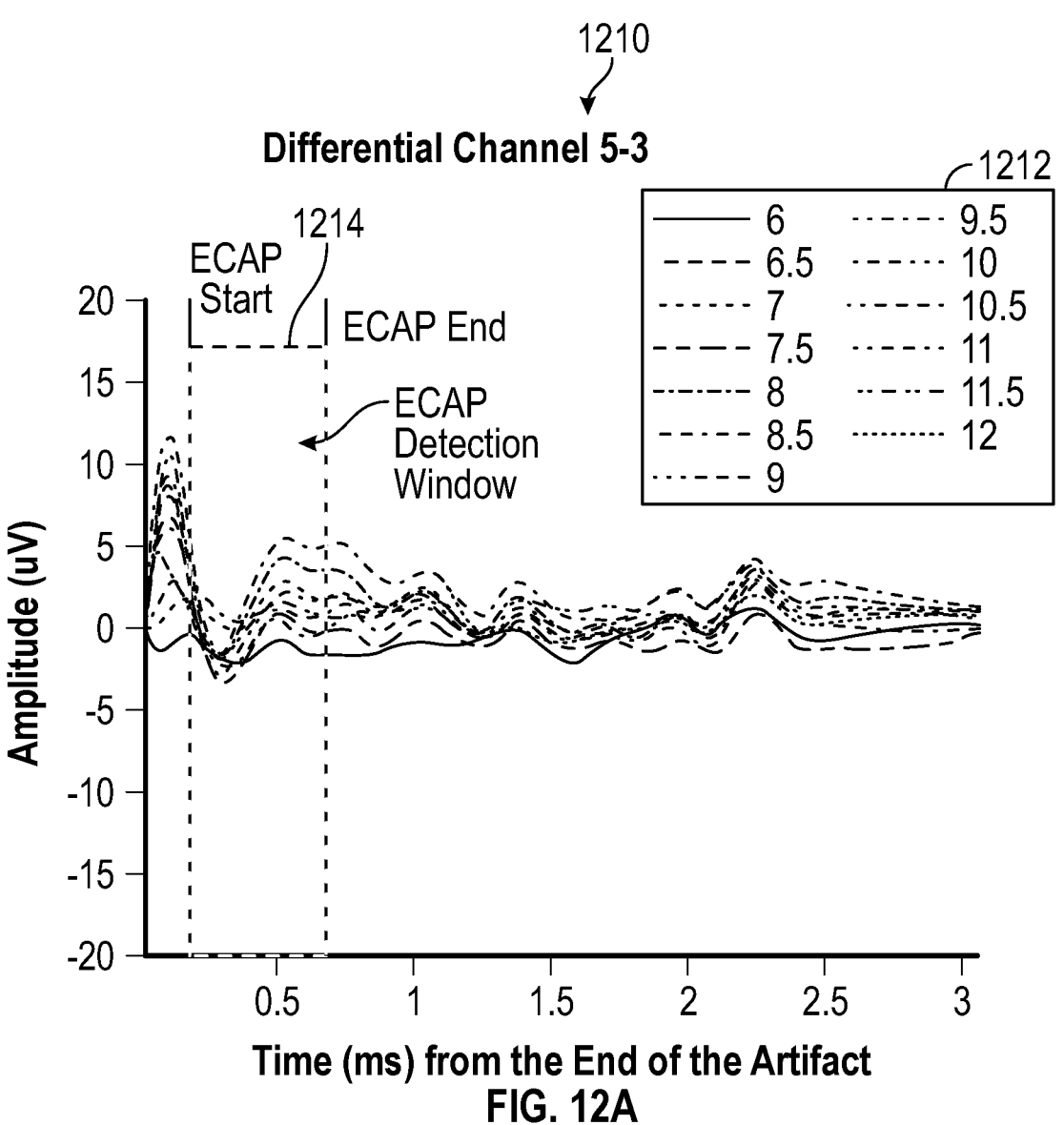
FIGS. 12A-12B illustrate another example of quality check of an evoked response signal based on patterns of inter-channel latencies under different stimulation current amplitudes.
Figure 12B:
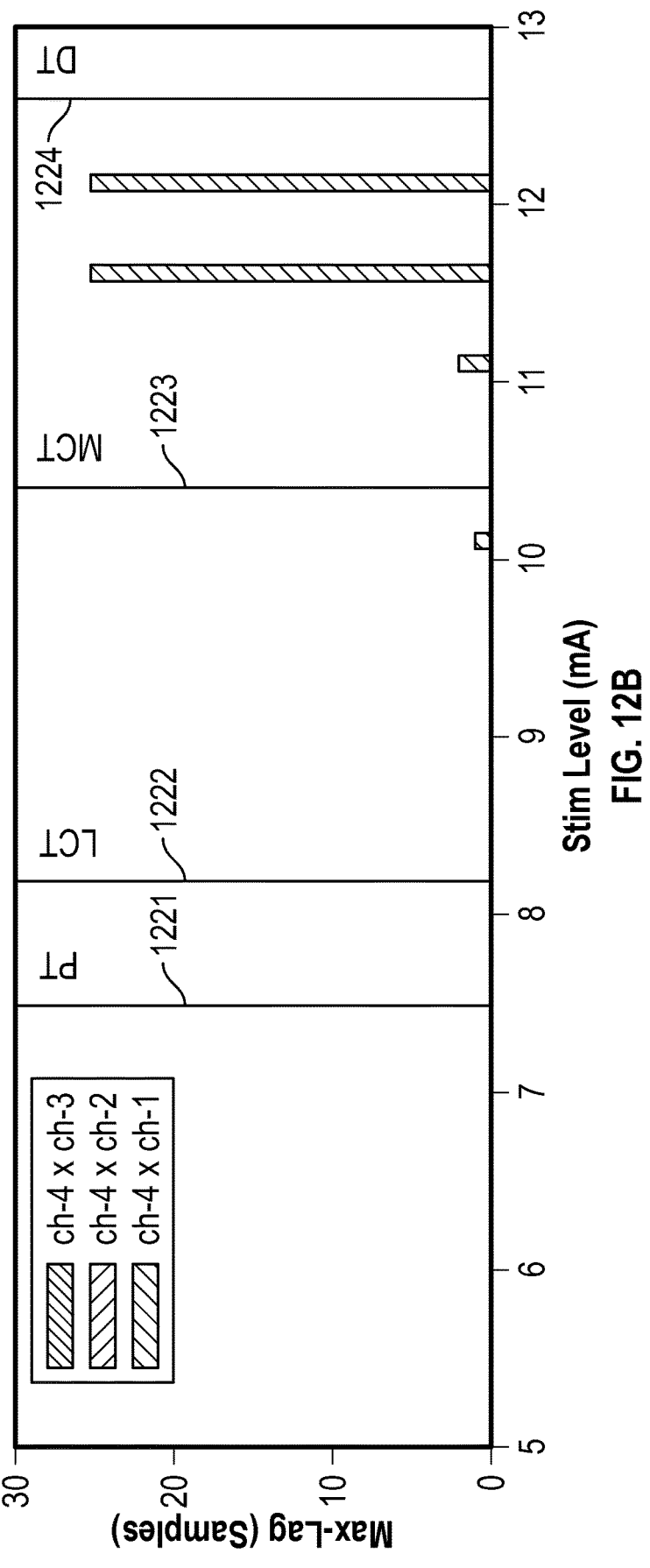

FIG. 12A illustrates another example of epoch-averaged ECAP signal segments 1210 calculated using ECAP signals sensed from a different patient via a different sense channel than the one used for generating the epoch-averaged ECAP signal segments 1110. The ECAP signals were sensed in response to stimulation at a number of stimulation current amplitudes 1212. FIG. 12B illustrates inter-channel latencies $L_{43}$, $L_{42}$, and $L_{41}$ each derived from respective cross-correlations of the averaged ECAP signal segments within a pre-determined or user-defined ECAP detection window 1214, under different stimulation current amplitudes. As discussed above, the signal quality check circuit 722 can determine whether the inter-channel latencies $L_{43}$, $L_{42}$, and $L_{41}$ form a particular pattern (e.g., an increasing trend) at a stimulation current amplitude above a particular threshold determined for the second sense channel, such as the PT 1221, LCT 1222, MCT 1223, or DT 1224. In contrast to the increasing trend $L_{43}$<$L_{42}$<$L_{41}$ as seen in FIG. 11B, no clear pattern of inter-channel latencies can be seen in FIG. 12B. Additionally, as stimulation current amplitudes increases, while the ECAP signal amplitude tends to increase (as shown in FIG. 12A), no consistent relationship between ECAP inter-channel latencies as seen across physically more distant sensing channels with respect to increasing stimulation amplitudes. Lack of a consistent pattern of inter-channel latencies across physically separated channels at increasing stimulation amplitudes also signifies non-physiological or non-propagating neural activities elicited by the stimulation. Since the waveforms in FIG. 12A have ECAP-like morphology, the inter-channel latency as discussed herein can help differentiate between physiological and propagating ECAPs and ECAP-like artifacts. Based on the absence of an inter-channel latency trend or the absence of a consistent pattern of inter-channel latencies with respect to increasing stimulation current amplitudes, the signal quality check circuit 722 can determine that, for certain stimulation current amplitudes, the sensed evoked response (e.g., any of the ECAP signal segments of channels 1 through 4) fails the quality check, and would not be automatically selected for evaluating neurostimulation effects and for closed-loop control of neurostimulation therapy.

Referring back to FIG. 7, the evoked response signal that passes a quality check (the "qualified" evoked response, as verified by the signal quality check circuit 722) can be provided to the feature extraction circuit 726 to extract a signal feature that may be used for evaluating neurostimulation effects and for closed-loop control of neurostimulation therapy. In an example, the feature extraction circuit 726 can determine an "optimal" feature (F*) from a plurality of candidate signal features (e.g., N candidate signal features $\{F_1, F_2, \ldots, F_N\}$) based on a predetermined performance criterion, and evaluate the optimal signal feature F* from the qualified evoked response. Examples of the candidate signal features can include a signal value range, a signal curve length, or a signal power of an evoked response signal within a time window, such as the epoch-averaged ECAP segments within the ECAP detection window, as shown in any of FIG. 10A, 11A, or 12A. The signal amplitude range or value range, also referred to as a peak-to-peak value, can be measured as a difference between a maximum value or a minimum value of the sensed evoked response (or an epoch-averaged ECAP segment) within the time window. The signal curve length can be measured as accumulated signal value differences of the sensed evoked response (or an epoch-averaged ECAP segment) over consecutive unit times (e.g., consecutive data sampling intervals) within the time window. The signal power can be measured as an area under the curve (AUC) of the sensed evoked response (or the epoch-averaged ECAP segment) within the time window.

The optimal signal feature (F*) can be selected from the plurality of candidate signal features based on respectively determined feature-indicated discrimination metric values $\{M_1, M_2, \ldots, M_N\}$ for the candidate signal features $\{F_1, F_2, \ldots, F_N\}$. A discrimination metric measures how well a candidate signal feature can distinguish between different electrostimulation therapy effects, such as between a first stimulation effect according to a first stimulation setting $(X_1)$ and a second stimulation effect according to a different second stimulation setting $(X_2)$. Examples of the stimulation setting can include stimulation current amplitude, pulse width, frequency, electrode configuration, current or energy fractionalization across electrodes, etc. In an example, the first stimulation setting includes a threshold stimulation intensity (e.g., current amplitude) capable of inducing maximum comfort in the patient, hereinafter referred to as maximum comfort threshold (MCT); and the second stimulation setting includes a threshold stimulation intensity (e.g., current amplitude) capable of inducing patient discomfort in the patient above a discomfort threshold (DT). In an example, the feature extraction circuit 726 can determine, for candidate signal feature $F_i$, a first statistical distribution $D_1(F_i)$ of values of $F_i$ in response to electrostimulation therapy delivered according to the first stimulation setting $(X_1)$, and a second statistical distribution $D_2(F_i)$ of values of $F_i$ in response to electrostimulation therapy delivered according to the second stimulation setting $(X_2)$. The statistical distribution $D_1(F_i)$ or $D_2(F_i)$ can be approximated by a histogram of sampled values of the candidate signal feature $F_i$ from respective evoked responses corresponding to respective stimulation settings $X_1$ and $X_2$. The feature extraction circuit 726 can evaluate, for candidate signal feature $F_i$, the discrimination metric $M_i$ that represents a degree of overlap between the statistical distributions $D_1(F_i)$ and $D_2(F_i)$. A higher degree of overlap indicates a poorer discriminatory performance of the candidate signal feature $F_i$ in distinguishing the first stimulation effect from the second stimulation effect, while a lower degree of overlap indicates a better discriminatory performance of the candidate signal feature $F_i$. The feature extraction circuit 726 can then select the optimal signal feature (F*) with the corresponding discrimination metric $M_i$ satisfying a specific selection criterion, such as exceeding a threshold value, or being greater than the discrimination metric values of other candidate signal features.

Various techniques may be used to calculate the discrimination metric for a candidate signal feature using the respective statistical distributions (e.g., $D_1(F_i)$ and $D_2(F_i)$) or histograms of the feature values under different stimulation settings $X_1$ and $X_2$. In one example, the discrimination metric can be determined using a Fischer's Linear Discriminant (FLD). The FLD is a classification method that projects high-dimensional data onto a line, and performs classification in this one-dimensional space. The projection maximizes the distance between the means of the two classes while minimizing the variance (or standard deviation) within each class. The FLD-based discrimination metric is correlated to a statistical distance between the distributions $D_1(F_i)$ and $D_2(F_i)$. Assuming, for candidate signal feature the feature value distribution $D_1(F_i)$ has a mean value of $m_1(F_i)$ and a standard deviation of $s_1(F_i)$, and the feature value distribution $D_2(F_i)$ has a mean value of $m_2(F_i)$ and a standard deviation of $s_2(F_i)$, then the FLD-based discrimination metric M can be determined using Equation (2) below:

$$M_i = (m_1(F_i) - m_2(F_i))^2 / (s_1(F_i)^2 + s_2(F_i)^2) \qquad (2)$$

In another example, the discrimination metric can be determined using a Jensen Shannon Divergence (JSD) metric. The JSD is a measure of the similarity between two probability distributions P and Q. The JSD is based on the Kullback-Leibler divergence that measures a relative entropy $D_{KL}(P\|Q)$ between the two probability distributions P and Q, which is defined as follows:

$$D_{KL}(P\|Q) = \sum_x P(x) \log \frac{P(x)}{Q(x)} \qquad (3)$$

For candidate signal feature $F_i$ and the feature value distributions $D_1(F_i)$ and $D_2(F_i)$, the JSD-based discrimination metric $M_i$ can be determined using Equations (4) and (5) below:

$$M_i = \tfrac{1}{2} D_{KL}(D_1(F_i)\|H(F_i)) + \tfrac{1}{2} D_{KL}(D_2(F_i)\|H(F_i)) \qquad (4)$$

$$H(F_i) = (D_1(F_i) + D_2(F_i))/2 \qquad (5)$$

Examples of statistical distributions of signal feature values and feature selection among candidate signal features based on discrimination metric such as FLD or JSD are discussed below with reference to FIGS. 13A-13C.

In some examples, the evoked response signal that passes the quality check (the "qualified" evoked response signal) can be pre-processed by the signal pre-processing circuit 725 before being passed to the feature extraction circuit 726. Alternatively, the evoked response signals received from the sensor circuit 710 can be first pre-processed by the signal pre-processing circuit 725, and the signal quality of the pre-processed evoked response signals can then be verified by the signal quality check circuit 722. The pre-processed evoked response signals that have passed the quality check can be fed into the feature extraction circuit 726 for feature extraction. The pre-processing of the sensed evoked response (or the qualified evoked response) may include, for example, filter settings for filtering the sensed evoked response signals, epoch averaging settings including number of epochs of the sensed evoked response to be averaged to produce an epoch-averaged evoked response signal, artifact treatment settings for avoiding or removing stimulation artifacts or other interfering biopotentials (e.g., ECG or EMG signals) from the evoked response signals, or feature window settings including defined time windows applied to the sensed evoked response signal to produce respective evoked response signal segments used for feature extraction.

Pre-processing of evoked responses or the qualified evoked response can affect feature selection by the feature extraction circuit 726. Appropriate pro-processing can improve quality of the evoked response and the discriminatory performance of the optimal signal feature F*, thereby improving the performance of closed-loop control of neuromodulation therapy. To determine an optimal pre-processing setting (e.g., one or more of an optimal filtering setting, an optimal epoch averaging setting, an optimal artifact treatment setting, or an optimal signal feature window setting), the signal pre-processing circuit 725 can pre-process the sensed evoked response (or the qualified evoked response) under a number of different candidate pre-processing settings. The feature extraction circuit 726 can extract a signal feature (e.g., a signal value range, a signal curve length, or a signal power such as AUC) from each of the pre-processed and qualified evoked response signals, and evaluate a pre-processing setting-indicated discrimination metric for the extracted feature. Examples of the discrimination metric can include FLD, JSD, or other measures of a degree of overlap between respective statistical distributions of feature values under two distinct stimulation settings $X_1$ and $X_2$, as discussed above. In contrast to the above discussion of feature selection from a plurality of candidate signal features based on evaluations of the feature-indicated discrimination metric, here the signal pre-processing circuit 725 can determine an optimal pre-processing setting based on the evaluations of the pre-processing setting-indicted discrimination metric. In an example, the optimal pre-processing setting can be selected as a candidate pre-processing setting with the corresponding pre-processing setting-indicted discrimination metric satisfying a specific selection criterion, such as exceeding a threshold value, or being greater than the pre-processing setting-indicted discrimination metric values of other candidate pre-processing settings. Examples of statistical distributions of signal feature values and pre-processing setting optimization based on discrimination metric such as FLD or JSD are discussed below with reference to FIGS. 13A-13C.

Factors such as evoked response sensing configuration may also affect feature selection by the feature extraction circuit 726. The sensing configuration can include anodes and cathodes designation, spacing between electrodes, sensing mode such as unipolar or bipolar sensing, etc. Appropriate sensing configuration, individually or together with appropriate pre-processing setting, can improve quality of the evoked response and the discriminatory performance of the optimal signal feature F*, thereby improving the performance of closed-loop control of neuromodulation therapy. To determine an optimal sensing configuration, the sensing configuration circuit 724 can sense respective evoked responses under a number of different candidate sensing configurations. The evoked responses each can be pre-processed (by the signal pre-processing circuit 725) and verified for signal quality (by the signal quality check circuit 722), and the feature extraction circuit 726 can extract a signal feature from each of the pre-processed and qualified evoked response signals, and evaluate a sensing configuration-indicated discrimination metric for the extracted feature. Examples of the discrimination metric can include FLD, JSD, or other measures of a degree of overlap between respective statistical distributions of feature values under two distinct stimulation settings $X_1$ and $X_2$, as discussed above. In contrast to the above discussion of feature selection from a plurality of candidate signal features based on evaluations of the feature-indicated discrimination metric, here the sensing configuration circuit 724 is to select an optimal sensing configuration based on evaluations of the sensing configuration-indicted discrimination metric. In an example, the optimal sensing configuration can be selected as a candidate sensing configuration with the corresponding sensing configuration-indicted discrimination metric satisfying a specific selection criterion, such as exceeding a threshold value, or being greater than the sensing configuration-indicted discrimination metric values of other candidate sensing configurations.

In addition to the discrimination metric derived from statistical distributions of candidate signal feature values under two distinct stimulating settings $X_1$ and $X_2$ as described above, in some examples, other considerations may be taken into account to determine or select an optimal signal feature (F*), an optimal pre-processing setting, or an optimal sensing configuration. Examples of such considerations include response time, computation complexity, or power consumption, among others. For example, to determine an optimal epoch number (i.e., the number of epochs of evoked response signal to be averaged), a high FLD- or JSD-based discrimination metric may be balanced against potential slower response and longer processing time as more epochs are averaged. In an example, the epoch number can be capped at a pre-determined upper limit (e.g., 15), and the optimal epoch number can be determined or selected as the lower value between the epoch number corresponding to a maximum discrimination metric value not exceeding the pre-determined upper limit. In another example, to determine an optimal artifact treatment setting, a high FLD- or JSD-based discrimination metric may be balanced against amount of computations and power requirement for performing such computations.

In some examples, determination or selection of an optimal signal feature (F*), an optimal pre-processing setting, or an optimal sensing configuration based on the statistical distributions of feature values can be implemented in training module. The training module can be included in the controller circuit 720 or another device or circuit other than the controller circuit 720. The training module can execute a training process to generate at least one trained model 732 that determines one or more of the optimal signal feature (F*), the optimal pre-processing setting, or the optimal sensing configuration using a training dataset comprising feature values under different stimulation settings. The at least one trained model 732 can be stored in a storage device 730. The sensing configuration circuit 724, the signal pre-processing circuit 725, and the feature extraction circuit 726 can all be communicatively coupled to the storage device 730. The sensing configuration circuit 724 can apply the optimal sensing configuration to the sensor circuit 710 to sense evoked response. The signal pre-processing circuit 725 can pre-process the sensed evoked response signal using the optimal pre-processing setting. The feature extraction circuit 726 can evaluate the optimal signal feature F* from the pre-processed and quality-checked evoked response signal. Examples of a system with such a training module for optimizing evoked response sensing and feature selection are discussed below with reference to FIG. 8.

In addition or alternative to optimization of signal feature (F*), sensing configuration, and evoked response pre-processing as discussed above, the FLD- or JSD-based discrimination metric may be used to optimize stimulation lead or electrode placement or other stimulation parameters (e.g., pulse amplitude, frequency, pulse width, or pulse waveform). For example, to determine an optimal stimulation parameter or stimulation electrode placement from a plurality of candidate stimulation parameters or electrode locations, evoked responses induced by electrostimulation therapies delivered in accordance with the plurality of candidate stimulation parameters or electrode locations can be acquired, and a signal feature (such as the optimal signal feature F*) can be evaluated (i.e., to determine the value of the signal feature) from each of the evoked responses. For each of the plurality of candidate stimulation parameters or electrode locations, the FLD- or JSD-based discrimination metric can be evaluated using the values of the target signal feature. Then, an optimal stimulation parameter or stimulation electrode can be determined as one the maximizes the FLD or JSD value among the plurality of candidate stimulation parameters or electrode locations (i.e., greater than the FLD or JSD values of any other candidate stimulation parameters or electrode locations).

The stimulation controller 728 can adjust stimulation settings based on the selected optimal signal feature. The electrostimulator 740 can deliver a neuromodulation therapy (e.g., SCS) in accordance with the adjusted stimulation setting. Examples of the stimulation setting may include, electrode selection and configuration, stimulation parameter values including, for example, amplitudes, pulse width, frequency, pulse waveform, active or passive recharge mode for FAST, ON time, OFF time, and therapy duration for BST, among others. In an example, the stimulation controller 728 can be implemented as a proportional integral (PI) controller, a proportional-integral-derivative (PID) controller, or other suitable controller that takes measurements of the selected signal feature (e.g., a "range" of epoch-averaged ECAP signal segments) as a feedback on the adjustment of stimulation settings. As the selected signal feature is optimized to distinguish between different therapy states such as an optimal therapy state and an avoidance state, the closed-loop feedback control based on the optimal signal feature can achieve more reliable paresthesia-free effects and improved patient outcome comprising the therapeutic effects of sub-perception electrostimulation.

The electrostimulator 740 can be an implantable module, such as incorporated within the IPG 10. Alternatively, the electrostimulator 740 can be an external stimulation device, such as incorporated with the ETS 40. In some examples, the user can choose to either send a notification (e.g., to the RC 45 or a smartphone with the patient) for a therapy reminder, or to automatically initiate or adjust stimulation therapy in accordance with the adjusted stimulation setting. If an automatic therapy initiation is selected, the electrostimulator 740 can deliver stimulation in accordance with the adjusted stimulation setting.

The user interface device 750 can be a portable (e.g., handheld) device, such as the RC 45 or a smartphone (with executable software application) operable by the patient at his or her home without requiring extra clinic visits or consultation with a device expert. In another example, the user interface device 750 can be a programmer device, such as the CP 50, that allows a physician to remotely review stimulation settings and treatment history, consult with the patient to obtain information including pain relief and SCS-related side effects or symptoms, perform remote programming of the electrostimulator 740, or provide other treatment options to the patient. The user interface device 750 can allow a user (e.g., the patient, the physician managing the patient, or a device expert) to view, program, or modify a device setting. For example, the user may use one or more user interface (UI) control elements to provide or adjust values of one or more device parameters, or select from a plurality of pre-defined stimulation programs for future use. Each stimulation program can include a set of stimulation parameters with respective pre-determined values. In some examples, the user interface device 750 can include a display to display textually or graphically information provided by the user via an input unit, and device settings including, for example, feature selection, sensing configurations, signal pre-processing settings, stimulation settings, optionally with any intermediate calculations (such as any of those shown FIGS. 8-12 for optimal signal feature selection or for signal quality check). In an example, the user interface device 750 may present to the user an "optimal" or improved stimulation setting, such as determined based on a closed-loop feedback control of electrostimulation based on a selected evoked response signal feature, in accordance with various embodiments discussed in this document.

In some examples, the user can use the interface device 750 to provide feedback on a stimulation therapy. The feedback provided by the user via the input unit can include pain data or feedback on pain relief by the existing SCS therapy. The pain data or the feedback on pain relief may include identification of pain sites, distribution of the pain, intensity of pain at various pain sites, or temporal pattern such as persistence of the pain at various pain sites, a pain drawing with pain markings identifying the locations, intensities, patterns of pain, among other information. In some examples, the feedback may include side effects or symptoms arise or persist associated with the SCS, or severity of the symptom or a side effect. The feedback can additionally include, for example, therapeutic effectiveness (e.g., pain relief) of a SCS program (e.g., FAST program), and symptoms or side effects experienced by the patient during the therapy. The feedback provided by the user can include pain data or feedback on pain relief by the existing SCS therapy. The pain data or the feedback on pain relief may include identification of pain sites, distribution of the pain, intensity of pain at various pain sites, or temporal pattern such as persistence of the pain at various pain sites, a pain drawing with pain markings identifying the locations, intensities, patterns of pain, among other information. In some examples, the feedback may include side effects or symptoms arise or persist associated with the SCS, or severity of the symptom or a side effect.

Although the description above with reference to FIG. 7 is focused on neurophysiological signals and particularly evoked responses, the techniques of using the discrimination metric (e.g., FLD or JSD) to optimize signal feature selection, sensing configuration (e.g., lead or electrode placement or other stimulation parameters), or signal pre-processing configuration can be similarly applied to a variety of physiological signals other than the evoked response signals as described above, including, for example, local field potentials (LFPs), or non-neurophysiological signals such as signals sensed using accelerometers, inertial measurement units, heart rate sensors, among others. The methods of discrimination metric (e.g., FLD or JSD) based signal feature selection and optimal sensing configuration may also be used in various applications of closed-loop control of therapy such as closed-loop deep brain stimulation (DBS). For example, algorithms based on discrimination metric (e.g., FLD or JSD) may look at various combinations of data length (amount of time to analyze signal over) and bandpass filter specifications (frequency range over which to extract a measure of band power) to determine a personalized signal filter configuration that can maximally distinguish different therapy or disease states. For example, when using signal power in a specific frequency band (e.g., the alpha band, typically 8-15 Hz), the discrimination metric (e.g., FLD or JSD) may determine a 8-12 Hz bandpass filter in one patient that optimally distinguishes therapy states A and B, while in another patient a 10-14 Hz bandpass filter would optimally distinguishes the therapy states A and B. Algorithms based on discrimination metric (e.g., FLD or JSD) may be similarly used to identify personalized optimal settings for other frequency-domain derived metrics to maximally distinguish different therapy or disease states, such as a phase-amplitude coupling (PAC), which relates to a coupling of the phase of slower electrophysiological oscillations with the amplitude of faster oscillations, a phenomenon that facilitates dynamic integration of neural activity in the brain.

Figure 8:
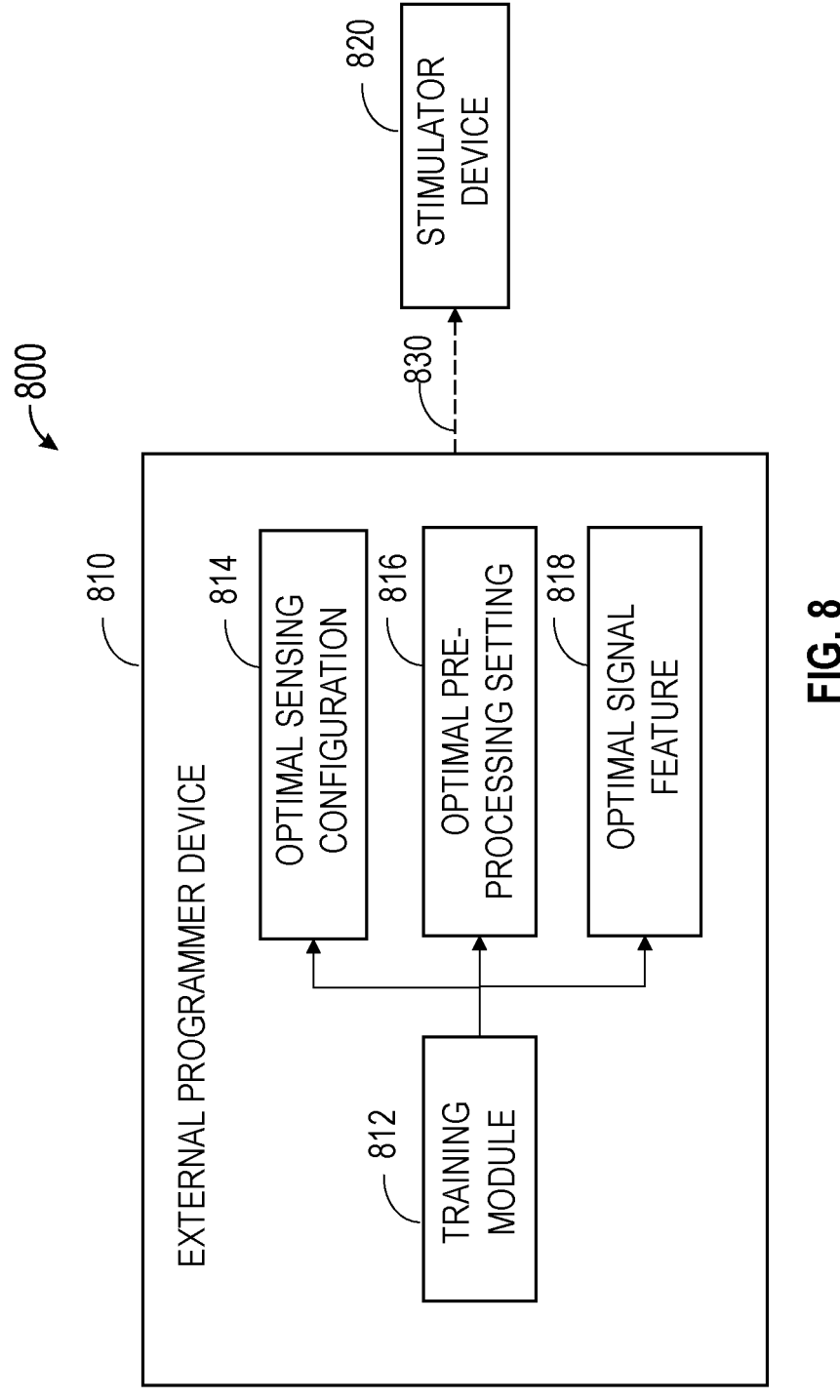
FIG. 8 illustrates an example of a neuromodulation system for optimizing evoked response sensing and signal feature selection from the evoked response using a trained model.

FIG. 8 illustrates an example neuromodulation system 800 for optimizing evoked response sensing and signal feature selection from the evoked response using a model trained by a training module 812. The neuromodulation system 800 comprises an external programmer device 810 (which can be, for example, the CP 50 or the RC 45), and a stimulator device 820 (which can be, for example, the IPG 10 or the ETS 40) communicatively coupled to the external programmer device 810. The training module 812 can be implemented in the external programmer device 810. One or more optimized parameters, such as an optimal sensing configuration 814, an optimal pre-processing setting 816, or an optimal signal feature (F*) 818, can be determined by the training module 812, as described above. Such optimized parameters can be exported to the stimulator device 820 via a communication link 830. The stimulator device 820 can sense evoked response using the optimal sensing configuration 814, pre-process the sensed evoked response using optimal pre-processing setting 816, and extract the optimal signal feature (F*) 818 (i.e., determine values of the optimal signal feature F*) from the pre-processed evoked response. The stimulator device 820 can evaluate electrostimulation therapy effectiveness or initiate closed-loop control of neuromodulation therapy based on the extracted optimal signal feature F*.

Figure 13A:
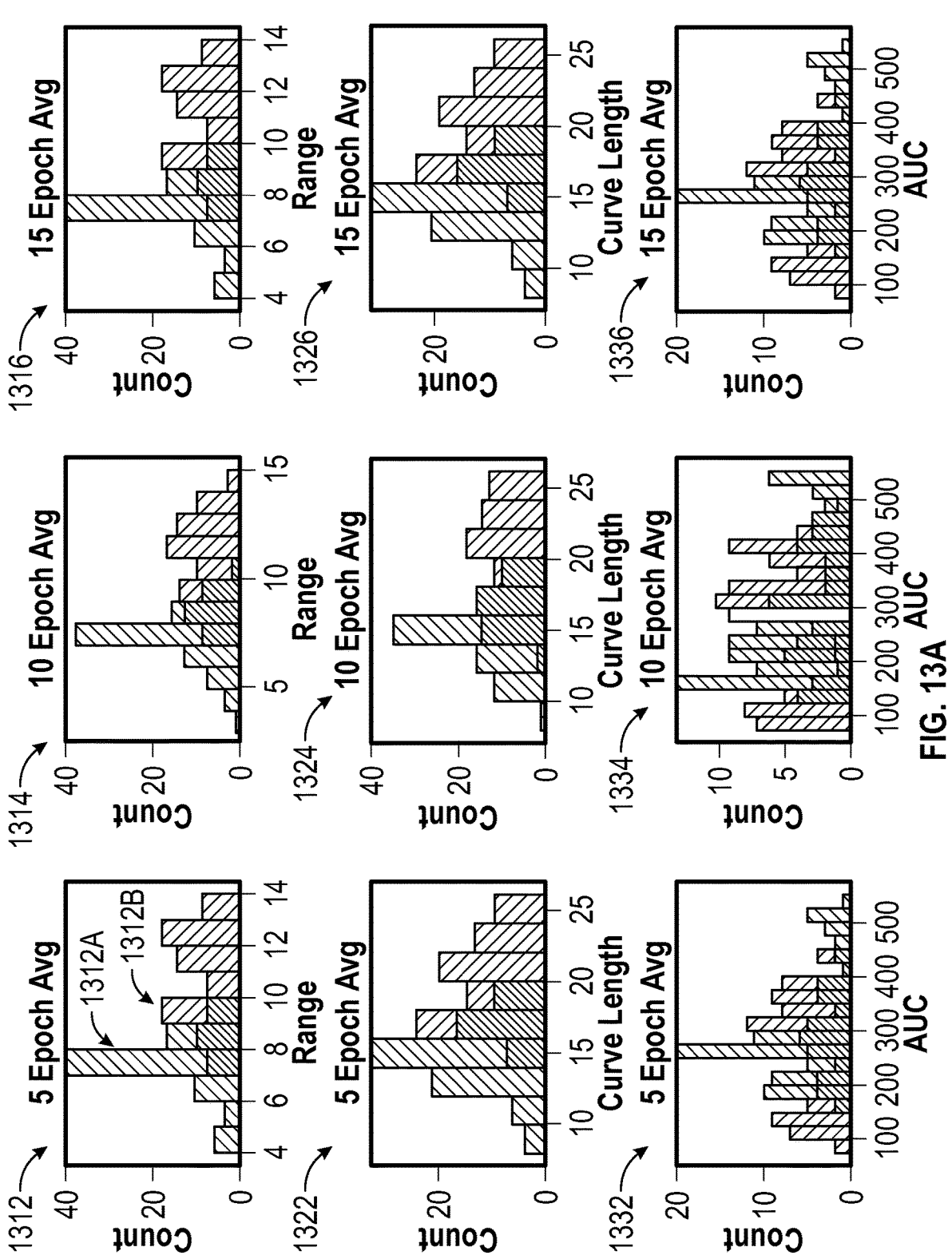
FIGS. 13A-13C illustrate examples of signal feature selection from a plurality of candidate signal features and pre-processing setting optimization among a plurality of candidate pre-processing settings based on statistical distributions of signal feature values obtained under different stimulation settings.
Figure 13B:
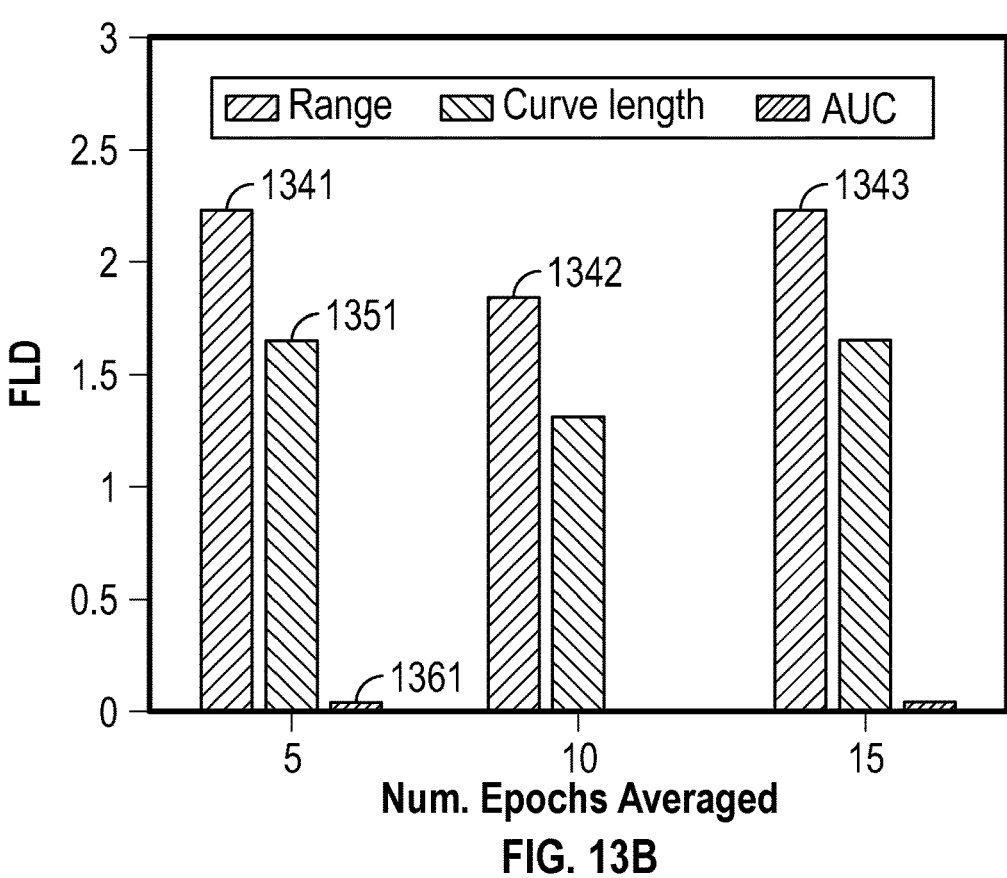
Figure 13C:
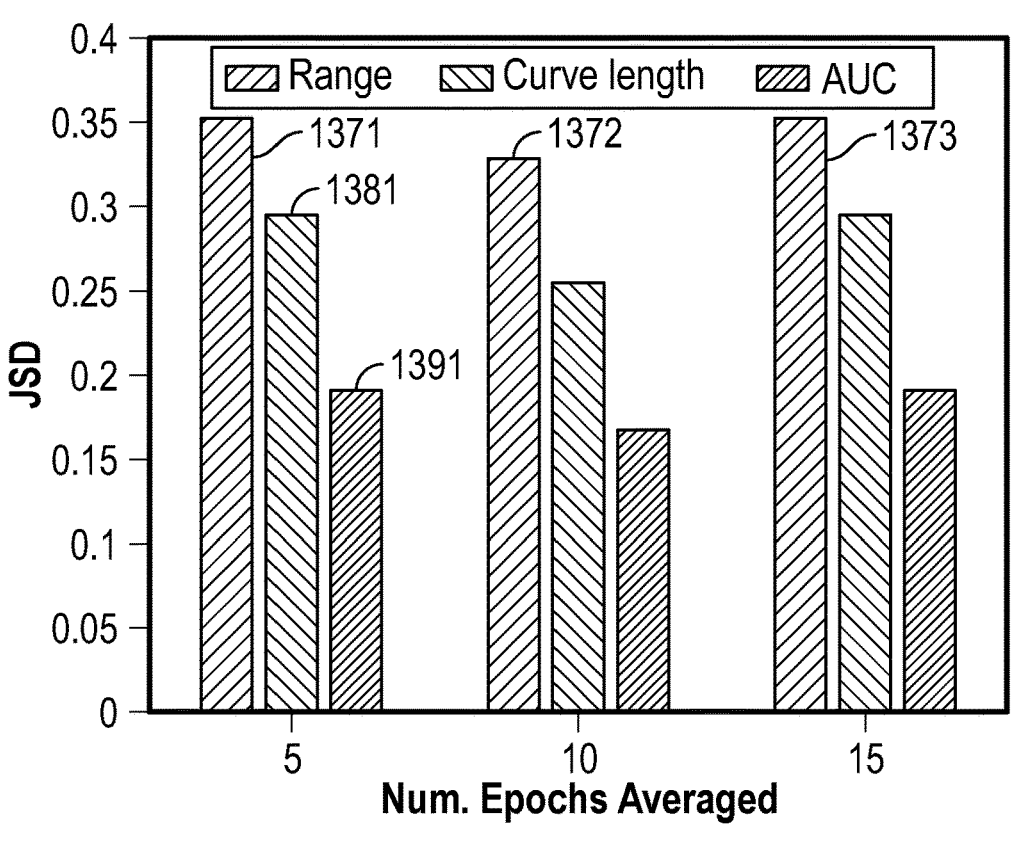

FIGS. 13A-13C illustrate examples of signal feature selection from a plurality of candidate signal features and pre-processing setting optimization among a plurality of candidate pre-processing settings based on statistical distributions of signal feature values obtained under different stimulation settings. Specifically, FIG. 13A illustrates examples of statistical distributions of a plurality of candidate signal features, including signal amplitude range ("Range"), signal curve length ("CL"), and signal power or area under the curve ("AUC"). As described above, the signal amplitude range, also referred to as a peak-to-peak value, can be measured as a difference between a maximum value or a minimum value of the sensed evoked response (or an epoch-averaged ECAP segment) within the time window. The signal curve length can be measured as accumulated signal value differences of the sensed evoked response (or an epoch-averaged ECAP segment) over consecutive unit times (e.g., consecutive data sampling intervals) within the time window. The signal power can be measured as an area under the curve (AUC) of the sensed evoked response (or the epoch-averaged ECAP segment) within the time window. The distributions of each candidate signal feature, as illustrated in FIG. 13A, can be approximated by histograms of sampled values of the respective candidate signal features obtained under two distinct stimulation settings, $X_{MCT}$ and $X_{DT}$. The first stimulation setting $X_{MCT}$ is capable of inducing maximum comfort in the patient above the maximum comfort threshold (MCT). The second stimulation setting $X_{DT}$ is capable of inducing patient discomfort in the patient above the discomfort threshold (DT). By way of example, diagram 1312 illustrates a histogram 1312A of "Range" values corresponding to stimulation setting $X_{MCT}$ and a histogram 1312B of "Range" values corresponding to stimulation setting $X_{DT}$. Similarly, diagram 1322 illustrates respective histograms of "CL" values under distinct stimulation settings $X_{MCT}$ and $X_{DT}$, and diagram 1332 illustrates respective histograms of "AUC" values under distinct stimulation settings $X_{MCT}$ and $X_{DT}$. To further determine an optimal pre-processing setting such as an optimal epoch averaging setting (e.g., an optimal number of epochs to be averaged), the candidate signal feature values can be measured from epoch-averaged ECAP signals averaged over 5, 10, or 15 epochs. In FIG. 13A, the "Range", "CL", and "AUC" values used for generating respective diagrams 1312, 1322, and 1332 are all measured from 5 epoch-averaged ECAP signals. The "Range", "CL", and "AUC" values used for generating respective diagrams 1314, 1324, and 1334 are all measured from 10 epoch-averaged ECAP signals. The "Range", "CL", and "AUC" values used for generating respective diagrams 1316, 1326, and 1336 are all measured from 15 epoch-averaged ECAP signals.

FIG. 13B illustrates FLD-based discrimination metric values for the "Range", the "CL", and the "AUC" features obtained from epoch-averaged ECAP signals averaged over 5, 10, or 15 epochs. The FLD can be calculated by applying the histogram data from FIG. 13A to Equation (2). In this example, at each epoch-average number, "Range" has a FLD-based discrimination metric value higher than CL and AUC. For example, for epoch number "5", the discrimination metric value for "Range" 1341 is greater than the discrimination metric value for "CL" 1351, which is greater than the discrimination metric value for "AUC" 1361. Accordingly, the feature extraction circuit 726 can select the "Range" feature as the optimal signal feature. Alternatively, the feature extraction circuit 726 can select any feature with a discrimination metric value exceeding a threshold value. Other considerations, such as response time, computation complexity, or power consumption, can additionally be taken into account in selecting the optimal signal feature.

FIG. 13B also illustrates how the discrimination metric of a signal feature would be affected by the epoch averaging settings, such as epoch numbers of 5, 10, and 15. In the illustrated example, for the "Range" feature, the discrimination metric value 1341 for epoch number "5" is comparable to the discrimination metric value 1343 for epoch number "15", both of which are higher than discrimination metric value 1342 for epoch number "10". Between the epoch numbers with comparable discrimination metric values, a lower epoch number (which is 5 in this example) can be determined as the optimal epoch number as it requires less computation time and fewer computation resources, and is more power efficient.

FIG. 13C illustrates JSD-based discrimination metric values for the "Range", the "CL", and the "AUC" features obtained from epoch-averaged ECAP signals averaged over 5, 10, or 15 epochs. The JSD can be calculated by applying the histogram data from FIG. 13A to Equations (3) through (5). In the illustrated example, for the "Range" feature, the discrimination metric value 1371 for epoch number "5" is comparable to the discrimination metric value 1373 for epoch number "15", both of which are higher than discrimination metric value 1372 for epoch number "10". At each epoch-average number, "Range" has a JSD-based discrimination metric value higher than CL and AUC. For example, for epoch number "5", the discrimination metric value for "Range" 1371 is greater than the discrimination metric value for "CL" 1381, which is greater than the discrimination metric value for "AUC" 1391. Accordingly, the feature extraction circuit 726 can select the "Range" feature as the optimal signal feature. Alternatively, the feature extraction circuit 726 can select any feature with a discrimination metric value exceeding a threshold value. Other considerations, such as response time, computation complexity, or power consumption, can additionally be taken into account in selecting the optimal signal feature.

FIG. 14 illustrates by way of example and not limitation a method 1400 for controlling an electrostimulation therapy delivered to a patient. Portions of the method 1400 may be implemented in and carried out by the neuromodulation system 700 or 800, or between one or more of the IPG 10, the ETS 40, or the CP 50.

At 1410, an evoked response may be sensed in response to an electrostimulation therapy delivered to a neural target of a patient by, for example, the electrostimulator 740 (e.g., included in the IPG 10) via an electrode lead, such as one or more leads 15. The electrostimulation therapy may be generated and delivered in accordance with one or more stimulation parameters. The evoked response can be sensed from one or more of a dorsal column, a dorsal root, or a peripheral nerve. In some examples, the evoked responses can be somatosensory evoked potential (SSEP) signal recorded by electrodes placed on patient scalp over the sensory area of the brain in response to stimulation of specific nerves in, for example, ankle, wrist, or other external body parts. In an example, a biopotential signal can be sensed by one or more subcutaneous electrodes. The biopotential signal can include an evoked potential or evoked compound action potential (ECAP).

At 1420, the sensed evoked response may be checked for signal quality, such as using the signal quality check circuit 722. One purpose of the quality check is to determine whether the evoked response represents a physiological and propagating neural activity elicited by the neurostimulation pulses, or non-physiological in nature, such as noise. In an example, the quality of the evoked response signal (e.g., a ECAP signal) may be verified based on a congruency (or a mismatch) between signal characteristics detected respectively using two or more different algorithms from the same evoked response signal. Examples of such signal characteristics can include a signal peak value (e.g., a maximum value or a minimum value), peak timing (e.g., respective timings of the signal maximum or signal minimum), peak-to-peak value (e.g., a difference between a maximum value or a minimum value, also referred to as an amplitude range or a value range), peak-to-peak duration (e.g., duration between the signal maximum or signal minimum), a signal curve length representing accumulated signal amplitude differences over consecutive unit times (e.g., consecutive data sampling intervals), or a signal power (e.g., an area under the curve of the evoked response signal), within a specific time window. In an example, a mismatch score can be computed using a weighted combination of the differences in a number of signal characteristics, according to Equation (1). If the mismatch score is lower than a threshold, then there is a high likelihood that the evoked response represents the physiological and propagating neural activity, such that the evoked response is determined to have passed the quality check.

The quality of the evoked response may alternatively be verified based on a cross-correlation between two evoked response signals sensed respectively from two distinct spatial locations with respect to the neural target being stimulated. The cross-correlation measures a similarity between the two evoked response signals at different time lags between the two signals. The sensed evoked response can be determined to have passed the quality check if the cross-correlation exceeds a threshold value. In an example, a latency (L) between the two evoked response signals can be determined from the cross-correlation therebetween. The latency (L) can be determined as the time lag for which the cross-correlation reaches a maximum. In some examples, cross-correlations may be computed using pairs of evoked responses sensed from different sense channels, and inter-channel latencies may be determined from respective cross-correlation. A pattern or a trend of the inter-channel latencies may be used to determine whether an evoked response has passed the quality check. For example, as described in the examples above with reference to FIGS. 10A-10B, 11A-11B, and FIGS. 12A-12B, an increasing trend of inter-channel latencies consistent with spatial locations of the sensing channels may indicate that the sensed evoked response has passed the quality check, and can automatically be selected for evaluating neurostimulation effects and for closed-loop control of neurostimulation therapy.

At 1430, a target signal feature (also referred to as an optimal signal feature F*) can be identified from a plurality of candidate signal features, such as using the feature extraction circuit 726. The target signal feature satisfies a performance criterion for distinguishing a first stimulation effect according to a first stimulation setting from a second stimulation effect according to a different second stimulation setting, and may be used for evaluating neurostimulation effects and for closed-loop control of neurostimulation therapy. The target signal feature can be selected based on respectively determined feature-indicated discrimination metric values for the candidate signal features. A discrimination metric measures how well a candidate signal feature can distinguish between different electrostimulation therapy effects, such as between a first stimulation effect according to a first stimulation setting and a second stimulation effect according to a different second stimulation setting. Examples of the stimulation setting can include stimulation current amplitude, pulse width, frequency, electrode configuration, current or energy fractionalization across electrodes, etc. In an example, the first stimulation setting includes a threshold stimulation intensity (e.g., current amplitude) capable of inducing maximum comfort in the patient, hereinafter referred to as maximum comfort threshold (MCT), and the second stimulation setting includes a threshold stimulation intensity (e.g., current amplitude) capable of inducing patient discomfort in the patient above a discomfort threshold (DT).

In an example, the first stimulation effect includes a first statistical distribution of a set of feature values in response to the stimulation therapy according to the first stimulation setting, and the second stimulation effect includes a second statistical distribution of a set of feature values in response to the stimulation therapy according to the second stimulation setting. A discrimination metric can be evaluated for each signal feature by determining a degree of overlap between the first statistical distribution and the second statistical distribution. Examples of the discrimination metric can include a Fischer's Linear Discriminant (FLD) and a Jensen Shannon Divergence (JSD) metric. A higher degree of overlap indicates a poorer discriminatory performance of a candidate signal feature in distinguishing the first stimulation effect from the second stimulation effect, while a lower degree of overlap indicates a better discriminatory performance of the candidate signal feature. The target signal feature can be identified as one with a corresponding discrimination metric satisfying a specific selection criterion, such as exceeding a threshold value, or being greater than the discrimination metric values of other candidate signal features. As an example of identifying the target signal feature using FLD- or JSD-based discrimination metric, FIGS. 13A-13C show that among the three candidate signal features "Range", "CL", and "AUC", the "Range" feature has a greater discrimination metric value (FLD value or JSD value) than "CL" and "AUC"; as such, the "Range" feature can be identified as the target or optimal signal feature In addition to the discrimination metric derived from statistical distributions of candidate signal feature values under two distinct stimulating settings as described above, in some examples, other considerations may be taken into account to determine or select a target signal feature, including, for example, response time, computation complexity, or power consumption, among others. For example, a high FLD- or JSD-based discrimination metric may be balanced against amount of computations and power requirement for performing such computations.

Sensing configuration and pre-processing of the sensed evoked response may also affect identification of a target or optimal signal features. The discrimination metric, such as FLD or JSD used for identifying a target signal feature as discussed above, may be used to identify a target sensing configuration from the plurality of candidate sensing configurations, or to identify a target signal pre-processing setting from a plurality of candidate signal pre-processing settings. In an example, a set of values of a specific signal feature (which can be the target or optimal signal feature, or a user-specified signal feature) can be determined from evoked responses sensed under each of the plurality of candidate sensing configurations. For each of the plurality of candidate sensing configurations, the discrimination metric (e.g., FLD or JSD) may be evaluated using the set of values of the specific signal feature. A target sensing configuration can be identified with a corresponding evaluated discrimination metric satisfying a specific condition, such as exceeding a threshold, or being the largest among the discrimination metric values of the candidate sensing configurations. An evoked response sensed in accordance with the target sensing configuration can be used in the feature selection process. For example, the value of the target signal feature F* may be determined from the evoked response sensed in accordance with the target sensing configuration.

In another example, a set of values of a specific signal feature (which can be the target or optimal signal feature, or a user-specified signal feature) can be determined from evoked responses pre-processed using each of the plurality of candidate signal pre-processing settings. For each of the plurality of candidate signal pre-processing settings, discrimination metric (e.g., FLD or JSD) can be evaluated using the set of values of the specific signal feature. A target signal pre-processing setting can be identified with a corresponding evaluated discrimination metric satisfying a specific condition, such as exceeding a threshold, or being the largest among the discrimination metric values of the candidate signal pre-processing settings. An evoked response pre-processed using the target signal pre-processing setting can be used in the feature selection process. For example, the value of the target signal feature F* may be determined from the evoked response pre-processed using the target signal pre-processing setting.

At 1440, the target signal feature F* can be evaluated using the sensed evoked response that has passed the quality check at 1420, that is, a value of the target signal feature can be determined from said evoked response. At 1450, based on the value of the target signal feature, a control signal can be generated to the electrostimulator to adjust the stimulation therapy. As the target signal feature is optimized to distinguish between different therapy states such as an optimal therapy state and an avoidance state, the closed-loop feedback control based on the target signal feature can achieve more reliable paresthesia-free effects and improved patient outcome comprising the therapeutic effects of sub-perception electrostimulation.

In some examples, some portions of the method 1400 (e.g., steps 1420 and/or 1430) can be performed in a training session such as using the training module 812 as described above with reference to FIG. 8, such that the criteria for signal quality check and/or the identification of target signal feature can be performed at the time of in-clinic setup or at diagnostic or troubleshooting sessions for the closed-loop algorithm with the assistive use of the external programmer device 810 (e.g., CP 50, RC 45, or other external devices). The training session may additionally include determining an optimal sensing configuration and evoked response pre-processing setting, as discussed above, After the training session, the identified optimal signal feature, the optimal sensing configuration, and the evoked response pre-processing setting can be stored in a memory and used continuously in future evoked response signal feature extraction and feedback-control of an electrostimulation therapy.

Figure 15:
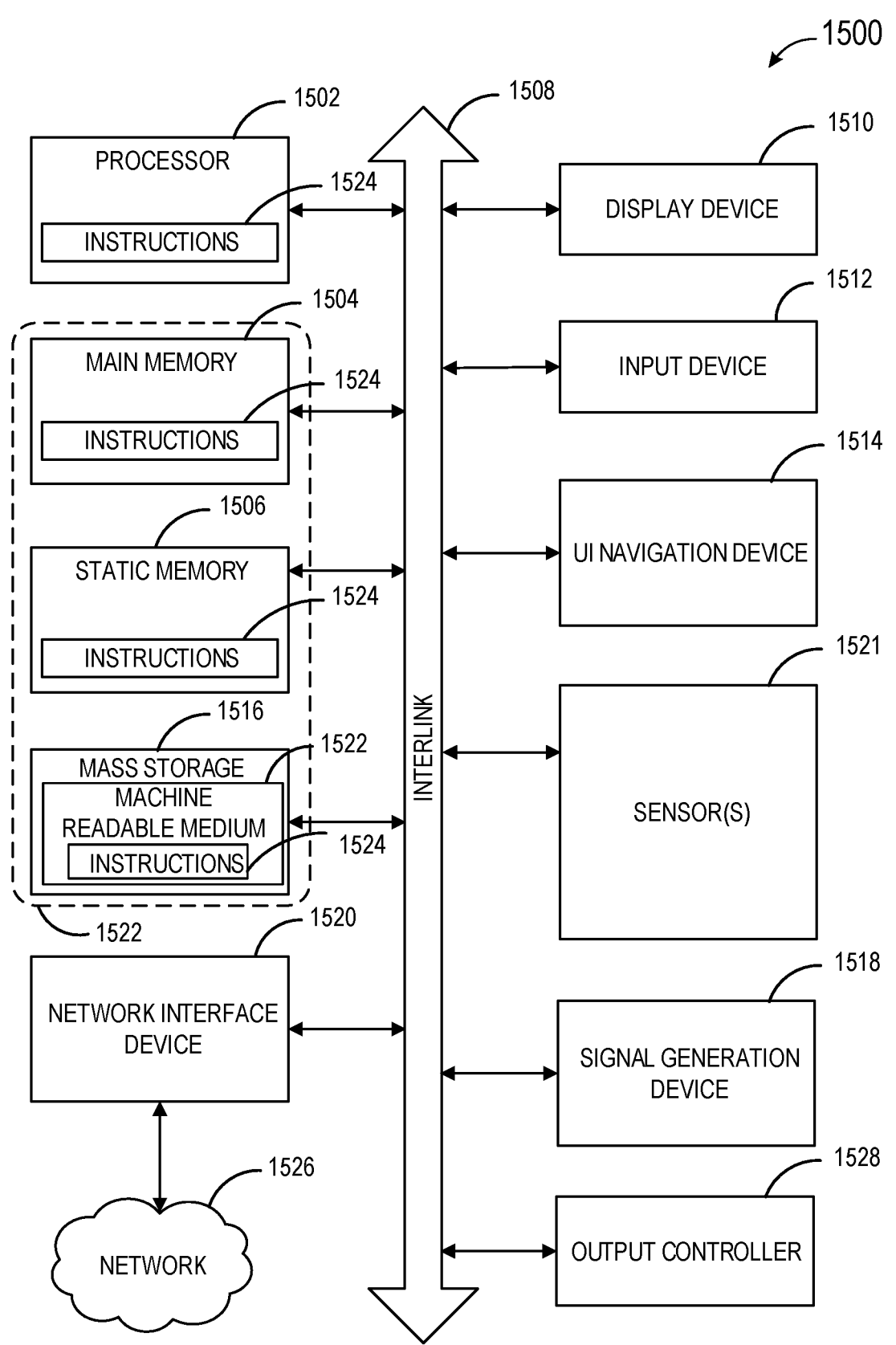
FIG. 15 illustrates generally a block diagram of an example machine upon which any one or more of the techniques (e.g., methodologies) discussed herein may perform.

FIG. 15 illustrates generally a block diagram of an example machine 1500 upon which any one or more of the techniques (e.g., methodologies) discussed herein may perform. Portions of this description may apply to the computing framework of various portions of the neuromodulation device or the external programming device as described in this document, such as those shown in FIG. 7 or FIG. 8.

In alternative examples, the machine 1500 may operate as a standalone device or may be connected (e.g., networked) to other machines. In a networked deployment, the machine 1500 may operate in the capacity of a server machine, a client machine, or both in server-client network environments. In an example, the machine 1500 may act as a peer machine in peer-to-peer (P2P) (or other distributed) network environment. The machine 1500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), among other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1500 may include a hardware processor 1502 (e.g., a central processing unit (CPU), a graphics processing unit (GPU), a hardware processor core, algorithm specific ASIC, or any combination thereof), a main memory 1504 and a static memory 1506, some or all of which may communicate with each other via an interlink (e.g., bus) 1508. The machine 1500 may further include a display unit 1510 (e.g., a raster display, vector display, holographic display, etc.), an alphanumeric input device 1512 (e.g., a keyboard), and a user interface (UI) navigation device 1514 (e.g., a mouse). In an example, the display unit 1510, input device 1512 and UI navigation device 1514 may be a touch screen display. The machine 1500 may additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensors. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1516 may include a machine readable medium 1522 on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media.

While the machine-readable medium 1522 is illustrated as a single medium, the term "machine readable medium" may include a single medium or multiple media (e.g., a centralized or distributed database, and/or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1524 may further be transmitted or received over a communication network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communication network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software.

Various examples are illustrated in the figures above. One or more features from one or more of these examples may be combined to form other examples.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for providing electrostimulation to a patient, the system comprising:

an electrostimulator configured to generate and deliver a stimulation therapy to a neural target of the patient;

a sensor circuit configured to sense an evoked response induced by the stimulation therapy delivered to the neural target; and a controller circuit configured to:

identify, from a plurality of candidate signal features, a target signal feature that satisfies a performance criterion for distinguishing (i) a first stimulation effect according to a first stimulation setting from (ii) a second stimulation effect according to a different second stimulation setting;

determine from the sensed evoked response a value of the target signal feature; and generate a control signal to the electrostimulator to adjust the stimulation therapy based on the value of the target signal feature, wherein to identify the target signal feature that satisfies the performance criterion, the controller circuit is configured to:

for each of the plurality of candidate signal features, determine a set of feature values from a set of evoked response signals, and evaluate a discrimination metric using the set of feature values, the discrimination metric measuring a performance of a candidate signal feature in distinguishing the first stimulation effect according to the first stimulation setting from the second stimulation effect according to the different second stimulation setting; and identify, from the plurality of candidate signal features, the target signal feature with a corresponding evaluated discrimination metric satisfying a specific condition.

2. The system of claim 1, wherein the plurality of candidate signal features of an evoked response signal include one or more of:

a signal amplitude range of within a specified time window;

a signal curve length representing accumulated signal amplitude differences over consecutive unit times within the specified time window; or a signal power within a specified time window.

3. The system of claim 1, wherein the first stimulation effect includes a first statistical distribution of the set of feature values in response to the stimulation therapy according to the first stimulation setting, and the second stimulation effect includes a second statistical distribution of the set of feature values in response to the stimulation therapy according to the second stimulation setting, wherein, to evaluate the discrimination metric for each of the plurality of candidate signal features, the controller circuit is configured to determine a degree of overlap between the first statistical distribution and the second statistical distribution.

4. The system of claim 3, wherein the discrimination metric includes a Fischer's Linear Discriminant (FLD) between the first statistical distribution and the second statistical distribution, wherein the controller circuit is configured to identify the target signal feature with a corresponding FLD value exceeding a threshold or being greater than FLD values of other of the plurality of candidate signal features.

5. The system of claim 3, wherein the discrimination metric includes a Jensen Shannon Divergence (JSD) metric between the first statistical distribution and the second statistical distribution, wherein the controller circuit is configured to identify the target signal feature with a corresponding JSD value exceeding a threshold or being greater than JSD values of other of the plurality of candidate signal features.

6. The system of claim 1, wherein the controller circuit is further configured to:

identify a target sensing configuration from a plurality of candidate sensing configurations, including:

determine a set of values of a specific signal feature from evoked responses sensed under each of a plurality of candidate sensing configurations;

for each of the plurality of candidate sensing configurations, evaluate a discrimination metric using the set of values of the specific signal feature, the discrimination metric measuring a performance of the specific signal feature in distinguishing the first stimulation effect according to the first stimulation setting from the second stimulation effect according to the different second stimulation setting; and identify the target sensing configuration with a corresponding evaluated discrimination metric satisfying a specific condition; and determine the value of the target signal feature using an evoked response sensed in accordance with the target sensing configuration.

7. The system of claim 1, wherein the controller circuit is configured to:

identify a target signal pre-processing setting from a plurality of candidate signal pre-processing settings, including:

determine a set of values of a specific signal feature from evoked responses pre-processed using each of a plurality of candidate signal pre-processing settings;

for each of the plurality of candidate signal pre-processing settings, evaluate a discrimination metric using the set of values of the specific signal feature, the discrimination metric measuring a performance of the specific signal feature in distinguishing the first stimulation effect according to the first stimulation setting from the second stimulation effect according to the different second stimulation setting; and identify the target signal pre-processing setting with a corresponding evaluated discrimination metric satisfying a specific condition; and determine the value of the target signal feature using an evoked response pre-processed using the target signal pre-processing setting.

8. The system of claim 7, wherein the plurality of candidate signal pre-processing settings include:

a plurality of signal filtering settings;

a plurality of epoch averaging settings; or a plurality of feature window settings.

9. The system of claim 1, wherein the controller circuit is further configured to:

perform a quality check on the sensed evoked response, including:

determine a congruency indicator between (i) a first value of a signal characteristic measured from the evoked response using a first algorithm and (ii) a second value of the signal characteristic measured from the evoked response using a second algorithm different than the first algorithm; and determine whether the sensed evoked response has passed the quality check based on the congruency indicator; and determine the value of the target signal feature using the sensed evoked response when the sensed evoked response passes the quality check.

10. The system of claim 1, wherein the controller circuit is further configured to:

perform a quality check on the sensed evoked response, including:

determine a cross-correlation between evoked responses sensed respectively from at least two different spatial locations with respect to the neural target; and determine whether the sensed evoked response has passed the quality check based on the cross-correlation; and determine the value of the target signal feature using the sensed evoked response when the sensed evoked response passes the quality check.

11. The system of claim 10, wherein the evoked responses are sensed respectively from at least three different spatial locations with respect to the neural target, wherein to perform the quality check, the controller circuit is configured to:

for each of a number of pairs of the evoked response, determine a cross-correlation therebetween and an inter-response latency using the cross-correlation; and determine whether the sensed evoked response has passed the quality check based on the inter-response latencies corresponding to the number of pairs of the evoked responses.

12. A method for providing electrostimulation to a patient, the method comprising:

sensing, via a sensor circuit, an evoked response induced by a stimulation therapy delivered to a neural target of the patient using an electrostimulator;

identifying, via a controller circuit, a target signal feature from a plurality of candidate signal features, the target signal feature satisfying a performance criterion for distinguishing (i) a first stimulation effect according to a first stimulation setting from (ii) a second stimulation effect according to a different second stimulation setting, wherein identifying the target signal feature includes (i) for each of the plurality of candidate signal features, determining a set of feature values from a set of evoked response signals, and evaluating a discrimination metric using the set of feature values, the discrimination metric measuring a performance of a candidate signal feature in distinguishing the first stimulation effect according to the first stimulation setting from the second stimulation effect according to the different second stimulation setting; and (ii) identifying, from the plurality of candidate signal features, the target signal feature with a corresponding evaluated discrimination metric satisfying a specific condition;

determining from the sensed evoked response a value of the target signal feature; and generating, via the controller circuit, a control signal to the electrostimulator to adjust the stimulation therapy based on the value of the target signal feature.

13. The method of claim 12, wherein the first stimulation effect includes a first statistical distribution of the set of feature values in response to the stimulation therapy according to the first stimulation setting, and the second stimulation effect includes a second statistical distribution of the set of feature values in response to the stimulation therapy according to the second stimulation setting, wherein evaluating the discrimination metric for each of the plurality of candidate signal features includes determining a degree of overlap between the first statistical distribution and the second statistical distribution.

14. The method of claim 13, wherein the discrimination metric includes a Fischer's Linear Discriminant (FLD) or a Jensen Shannon Divergence (JSD) between the first statistical distribution and the second statistical distribution, and the target signal feature is identified to have a corresponding FLD value or a JSD value exceeding a threshold or being greater than FLD values or JSD values of other of the plurality of candidate signal features.

15. The method of claim 12, further comprising:

determining a set of values of a specific signal feature from evoked responses sensed under each of a plurality of candidate sensing configurations;

for each of the plurality of candidate sensing configurations, evaluating a discrimination metric using the set of values of the specific signal feature, the discrimination metric measuring a performance of the specific signal feature in distinguishing the first stimulation effect according to the first stimulation setting from the second stimulation effect according to the different second stimulation setting;

identifying, from the plurality of candidate sensing configurations, a target sensing configuration with a corresponding evaluated discrimination metric satisfying a specific condition; and determining the value of target signal feature using an evoked response sensed in accordance with the target sensing configuration.

16. The method of claim 12, further comprising:

identifying a target signal pre-processing setting from a plurality of candidate signal pre-processing settings; and determining the value of the target signal feature using an evoked response pre-processed using the target signal pre-processing setting;

wherein identifying the target signal pre-processing setting includes:

determining a set of values of a specific signal feature from evoked responses pre-processed using each of the plurality of candidate signal pre-processing settings;

for each of the plurality of candidate signal pre-processing settings, evaluating a discrimination metric using the set of values of the specific signal feature, the discrimination metric measuring a performance of the specific signal feature in distinguishing the first stimulation effect according to the first stimulation setting from the second stimulation effect according to the different second stimulation setting; and identifying, from the plurality of candidate signal pre-processing settings, the target signal pre-processing setting with a corresponding evaluated discrimination metric satisfying a specific condition.

17. The method of claim 12, comprising:

performing, via the controller circuit, a quality check on the sensed evoked response, including:

determining a congruency indicator between (i) a first value of a signal characteristic measured from the evoked response using a first algorithm and (ii) a second value of the signal characteristic measured from the evoked response using a second algorithm different than the first algorithm; and determining whether the sensed evoked response has passed the quality check based on the congruency indicator; and determining the value of the target signal feature using the sensed evoked response when the sensed evoked response passes the quality check.

18. The method of claim 12, comprising:

performing, via the controller circuit, a quality check on the sensed evoked response, including:

determining a cross-correlation between evoked responses sensed respectively from at least two different spatial locations with respect to the neural target; and determining whether the sensed evoked response has passed the quality check based on the cross-correlation; and determining the value of the target signal feature using the sensed evoked response when the sensed evoked response passes the quality check.

* * * * *